US009939381B1

United States Patent
Kimmel et al.

(10) Patent No.: US 9,939,381 B1
(45) Date of Patent: Apr. 10, 2018

(54) AUTOMATED SCANNING PATH PLANNER WITH PATH CALIBRATION FOR HIGH FRAME RATE MULTI PHOTON LASER SCANNING MICROSCOPE WITH WIDE FIELD OF VIEW

(71) Applicant: VIDRIO TECHNOLOGIES, LLC, Ashburn, VA (US)

(72) Inventors: Bruce Kimmel, Ashburn, VA (US); Jonathan King, Ashburn, VA (US); Nathan Clack, Ashburn, VA (US); Georg Jaindl, Ashburn, VA (US)

(73) Assignee: VIDRIO TECHNOLOGIES, LLC, Ashburn, VA (US)

( * ) Notice: Subject to any disclaimer, the term of this patent is extended or adjusted under 35 U.S.C. 154(b) by 0 days.

(21) Appl. No.: 15/481,476

(22) Filed: Apr. 7, 2017

(51) Int. Cl.
| | |
|---|---|
| *G01N 21/64* | (2006.01) |
| *G02B 21/00* | (2006.01) |
| *G02B 21/02* | (2006.01) |
| *G02B 21/16* | (2006.01) |

(52) U.S. Cl.
CPC ....... *G01N 21/6458* (2013.01); *G02B 21/002* (2013.01); *G02B 21/02* (2013.01); *G02B 21/16* (2013.01); *G01N 2021/6478* (2013.01); *G01N 2201/105* (2013.01); *G01N 2201/127* (2013.01)

(58) Field of Classification Search
CPC ....... G01N 21/6458; G01N 2021/6478; G01N 2201/105; G01N 2201/127; G02B 21/002; G02B 21/02; G02B 21/16
See application file for complete search history.

(56) References Cited

U.S. PATENT DOCUMENTS

| | | | | |
|---|---|---|---|---|
| 2009/0067458 A1* | 3/2009 | Ji | ............ | H01S 3/0057 |
| | | | | 372/25 |
| 2010/0049055 A1* | 2/2010 | Freudenberg | ........ | A61B 5/0059 |
| | | | | 600/475 |
| 2010/0328759 A1* | 12/2010 | Kirkby | ............... | G01N 21/6458 |
| | | | | 359/310 |
| 2012/0140301 A1* | 6/2012 | Xu | ........ | G02B 23/243 |
| | | | | 359/198.1 |
| 2013/0324858 A1* | 12/2013 | Xu | ........ | G01N 21/645 |
| | | | | 600/478 |
| 2014/0023993 A1* | 1/2014 | Zeng | .......... | G02B 21/0052 |
| | | | | 433/215 |
| 2016/0238532 A1* | 8/2016 | Freudiger | .......... | G01N 21/6402 |
| 2016/0302740 A1* | 10/2016 | Iyer | ........ | A61B 5/748 |
| 2016/0310319 A1* | 10/2016 | Friedman | .............. | A61F 9/0079 |
| 2016/0338588 A1* | 11/2016 | Friedman | .............. | A61B 3/145 |
| 2017/0021021 A1* | 1/2017 | Kamaev | ........ | A61F 9/0079 |
| 2017/0102532 A1* | 4/2017 | Frankel | .............. | G02B 21/0076 |
| 2017/0156926 A1* | 6/2017 | Friedman | .............. | A61F 9/0026 |

* cited by examiner

*Primary Examiner* — Mark R Gaworecki
(74) *Attorney, Agent, or Firm* — Todd Juneau; Juneau & Mitchell

(57) ABSTRACT

The invention relates to multi-photon excitation microscopy, and in particular to a path planning module and calibration module for three mirror adaptive sampling system configured to automatically generate an optimized RGG mirror scanning path by scanning a Field of View, identifying multiple region of interest targets, and analyzing the targets to generate an optimized path. The invention also relates to methods for maintaining a high frame rate during wide field of view sampling.

18 Claims, 12 Drawing Sheets

AUTOMATED SCANNING PATH PLANNER WITH PATH CALIBRATION FOR HIGH FRAME RATE MULTI PHOTON LASER SCANNING MICROSCOPE WITH WIDE FIELD OF VIEW

CROSS REFERENCE TO RELATED APPLICATIONS

STATEMENT REGARDING FEDERALLY SPONSORED RESEARCH

NAMES OF PARTIES TO JOINT RESEARCH AGREEMENT

BACKGROUND

Field of the Invention

The invention relates to multi-photon excitation microscopy, and in particular to a planner and calibration module for a multi-mirror adaptive sampling system configured to maintain a high frame rate during wide field of view sampling.

Background of the Invention

In laser scanning microscopy, a laser is directed at a sample such as animal tissue and an image is acquired one pixel at a time. Two-photon excitation microscopy is a fluorescence imaging technique that allows three-dimensional imaging of living tissue up to about one millimeter in depth. In contrast to confocal laser scanning microscopy, it does not require a focal diaphragm. Being a special variant of the fluorescence microscope, it uses red-shifted excitation light to excite fluorescent dyes causing an emission of photons. However, for each excitation, two photons of infrared light are absorbed. Using infrared light minimizes scattering in the tissue. Due to the multiphoton absorption, the background signal is strongly suppressed. Both effects lead to an increased penetration depth for these microscopes. Two-photon excitation, and now three-photon excitation, can be a superior alternative to confocal microscopy due to its deeper tissue penetration, efficient light detection, and reduced phototoxicity.

SUMMARY

Automated Planner and Adaptive Sampling System

In a preferred embodiment, the invention provides an automated planner and adaptive sampling system for multi-photon excitation microscopy, comprising:
(a) a full frame scanner module configured to scan an entire Field of View (FOV) of a specimen and label a detailed high resolution image with multiple Region of Interest (ROI) targets within the FOV;
(b) a segmentation module configured to save an X-Y-Z coordinate for each ROI target;
(c) an acquisition planner module configured to analyze the X-Y-Z coordinates for each ROI target, and generate an optimized mirror scanning path for the laser to intersect each ROI target;
(d) an acquisition fluorescence sampling module configured to use the optimized mirror scanning path and record a fluorescence signal from each ROI target in the FOV;
(e) a data viewing module configured to present in real time two views with a graphical user interface, a first view comprises a plot of intensity over time of the fluorescent signals from each ROI target, and a second view comprises a live presentation of the optimized mirror scanning path over time period t with each ROI target in the FOV colored by an intensity of fluorescence according to the fluorescent signal last measured at a previous time period t−1;
(f) a multi-photon excitation microscope for multi-region of interest (MROI) imaging of intact cellular tissue comprising:
  (i) a laser configured for multi-photon laser spectroscopy;
  (ii) a Pockels cell operatively associated with the laser to control laser power;
  (iii) one or more focusing lenses in optical communication with the laser;
  (iv) a compact scanner assembly in optical communication with the laser;
  (v) one or more dichroic mirrors in optical communication with the laser;
  (vi) one or more objective lenses in optical communication with the laser;
  (vii) one or more photomultiplier tubes in optical communication with the FOV;
  (viii) a computer comprising one or more processors, memory, storage memory, interfaces, controllers, and input devices for operating the multi-photon excitation microscope, said computer having a display for receiving the graphical user interface; wherein the modules comprise computer program instructions executable by the one or more processors.

In a non-limiting preferred embodiment, the compact scanner assembly comprises a GG scanner assembly, an RG scanner assembly, an RGG scanner assembly, and RGGG scanner assembly, an RGGGG scanner assembly, or a MEMS mirror scanner assembly.

In a non-limiting preferred embodiment, the compact scanner assembly comprises a resonant scanner (R) driven at a resonant frequency selected from 8 KHz, 12 KHz, and 16 KHz, a first galvanometer scanner (G1), and a second galvanometer scanner (G2).

In a non-limiting preferred embodiment, the multi-photon excitation microscope is a two-photon excitation microscope.

In a non-limiting preferred embodiment, the a multi-photon excitation microscope is a three-photon excitation microscope.

In another non-limiting preferred embodiment, there is provided an automated planner and adaptive sampling system wherein the Frame Rate during wide field of view sampling comprises a range selected from the group of ranges consisting of: Frame Rate range 60 Hz-200 Hz, Frame Rate range 100 Hz-200 Hz, Frame Rate range 100 Hz-500 Hz, Frame Rate range 200 Hz-500 Hz, Frame Rate range 200 Hz-1000 Hz, Frame Rate range 100 Hz-2000 Hz, Frame Rate range 200 Hz-2000 Hz, Frame Rate range 500 Hz-2000 Hz, Frame Rate range 500 Hz-1200 Hz, Frame Rate range 500 Hz-1500 Hz, and Frame Rate range 500 Hz-2000 Hz.

In another non-limiting preferred embodiment, there is provided an automated planner and adaptive sampling system that further comprises a path adjustment module, said path adjustment module configured to provide a path correction input to change the coordinates of one or more ROI targets within the optimized mirror scanning path.

In another non-limiting preferred embodiment, there is provided an automated planner and adaptive sampling system that further comprises an automated calibration module configured to generate and save coordinates of an actual mirror scanning path and compare the coordinates of the actual mirror scanning path to the coordinates of the optimized mirror scanning path while a scan is in progress, said automated calibration module configured to adjust the coordinates of the actual mirror scanning path to match the coordinates of the optimized mirror scanning path.

In another non-limiting preferred embodiment, there is provided an automated planner and adaptive sampling system that further comprises an automated calibration module configured to generate and save coordinates of an actual mirror scanning path and compare the coordinates of the actual mirror scanning path to the coordinates of an updated optimized mirror scanning path while a scan is in progress, said automated calibration module configured to re-scan an entire Field of View (FOV) of a specimen, re-label a detailed high resolution image with multiple Region of Interest (ROI) targets within the FOV, re-save an X-Y-Z coordinate for each ROI target, re-analyze the X-Y-Z coordinates for each ROI target, and generate an updated optimized mirror scanning path for the laser to intersect each ROI target, said automated calibration module configured to adjust the coordinates of the actual RGG mirror scanning path to match the coordinates of the updated optimized mirror scanning path.

In another non-limiting preferred embodiment, there is provided an automated planner and adaptive sampling system that further comprises a Scanner Status Module configured to generate and save scanner variables while a scan is in progress, said scanner variables comprising scanner motion and scanner orientation for each scanner for each ROI target within a FOV, said Scanner Status Module configured to generate a Scanner Status Report output to the graphical user interface.

In another non-limiting preferred embodiment, there is provided an automated planner and adaptive sampling system that further comprises a Variable Priority Module configured to generate and save Sampling Variables selected from vertical resolution, horizontal resolution, frame rate, ROI threshold, and laser power, said Variable Priority Module configured to adjust the optimized RGG mirror scanning path for each ROI target within a FOV based on user-selected priority settings of the Sampling Variables, said Variable Priority Module configured to generate a Variable Priority Status Report output to the graphical user interface.

In another non-limiting preferred embodiment, there is provided an automated planner and adaptive sampling system that further comprises an automated threshold trigger module, said automated threshold trigger module configured to add coordinates of one or more ROI targets within the optimized mirror scanning path based on a triggering event, said automated threshold trigger module further configured to generate and save a series of image Frames based on the triggering event.

In another non-limiting preferred embodiment, there is provided an automated planner and adaptive sampling system wherein the laser is a femtosecond laser with an emitted wavelength range 680-1400 nm.

In another non-limiting preferred embodiment, there is provided an automated planner and adaptive sampling system wherein the laser is a femtosecond laser with an emitted wavelength range 760-1100 nm.

In another non-limiting preferred embodiment, there is provided an automated planner and adaptive sampling system wherein the compact scanner assembly comprises a set of three electromagnetically actuated scanning mirrors in optical communication with the laser, comprising in sequence a first galvanometer scanner (G1) having a mirror (m1), a resonant scanner (R) driven at a resonant frequency selected from 8 KHz, 12 KHz, and 16 KHz, and a second galvanometer scanner (G2) having a mirror (m2), wherein the first galvanometer scanner (G1) and the second galvanometer scanner (G2) are driven by a lower bandwidth control signal specifying an angle for mirror (m1) and for mirror (m2), wherein the set of three scanning mirrors are within a single scanner assembly (RGG), wherein spacing between the first galvanometer scanner (G1) and the resonant scanner (R) ranges from 4.0-12.0 mm, and wherein spacing between the resonant scanner (R) and the second galvanometer scanner (G2) ranges from 4.0-12.0 mm.

In another non-limiting preferred embodiment, there is provided an automated planner and adaptive sampling system that further comprises a third galvanometer scanner (G3) and mirror (m3) within the single scanner assembly (RGGG), wherein the third galvanometer scanner (G3) is driven by a lower bandwidth control signal specifying an angle for mirror (m3), wherein spacing between the second galvanometer scanner (G2) and the third galvanometer scanner (G3) ranges from 4.0-12.0 mm.

In another non-limiting preferred embodiment, there is provided an automated planner and adaptive sampling system wherein the electromagnetically actuated scanning mirrors are controlled by a Piezo/Fast Z control module for controlling the position of the mirrors, and the scanning mirrors are actuated by one or more piezoactuators selected from the group consisting of: a multilayer stack piezoactuator, a monolithic piezoactuator, a tube piezoactuator, a multilayer ring piezoactuator, a bimorph piezoactuator, and a hybrid piezoactuator.

In another non-limiting preferred embodiment, there is provided an automated planner and adaptive sampling system that further comprises an Equipment Control Module (ECM), said ECM comprising:

i) a laser power control unit and a laser wavelength output control in operative association with the laser; and ii) a galvanometer 1 control, a resonant mirror control, and a galvanometer 2 control in operative association with the scanning mirrors.

In another non-limiting preferred embodiment, there is provided an automated planner and adaptive sampling system that further comprises a Data Acquisition Module (DAQ), said DAQ comprising a frame rate control module, a scan mode control module, a scan zoom control module, and a data acquisition pixel density control module in operative association with the DAQ.

In another non-limiting preferred embodiment, there is provided an automated planner and adaptive sampling system that further comprises a dichroic mirror light path adjustment module in operative association with the one or more dichroic mirrors.

In another non-limiting preferred embodiment, there is provided an automated planner and adaptive sampling system wherein the one or more dichroic mirrors is positioned after the scanning mirrors in optical communication with the laser, wherein the dichroic mirrors are reflective at a first lower wavelength, and the mirrors are transmissive at a second wavelength higher than the first wavelength.

In another non-limiting preferred embodiment, there is provided an automated planner and adaptive sampling system wherein the one or more dichroic mirrors are reflective at a wavelength of less than 680 nm, and the mirrors are transmissive at a wavelength ranging from 680-1400 nm.

In another non-limiting preferred embodiment, there is provided an automated planner and adaptive sampling system wherein the one or more dichroic mirrors are reflective at a wavelength of less than 760 nm, and the mirrors are transmissive at a wavelength ranging from 760-1100 nm.

In another non-limiting preferred embodiment, there is provided an automated planner and adaptive sampling system, wherein the one or more objective lenses have a pupil diameter from 10-30 mm configured to output the emitted laser to interact with a specimen, and configured to receive an excitation illumination at the second wavelength.

In another non-limiting preferred embodiment, there is provided an automated planner and adaptive sampling system wherein the one or more photomultiplier tubes comprise at least two non-descanned Photo Multiplier Tubes configured to receive excitation illumination and configured with a transimpedance amplifier to transmit image data thru a controller interface to a Data Acquisition Module.

In another non-limiting preferred embodiment, there is provided an automated planner and adaptive sampling system wherein the Data Acquisition (DAQ) Module has a channel digitizer having from 2-32 channels, an Field Programmable Gate Array (FPGA) module, and a Pockels control module.

In another non-limiting preferred embodiment, there is provided an automated planner and adaptive sampling system wherein the computer is connected to the DAQ, the computer comprising a central processing unit (CPU) configured to process in 64-bit, in Quad-core and 3.5 GHZ or better, Random Access Memory (RAM) at least 8 GB, a Graphics Processing Unit (GPU), two or more PCIe slots, and a storage memory comprising an Solid State Drive (SSD) or a Hard Drive.

In another non-limiting preferred embodiment, there is provided an automated planner and adaptive sampling system that further comprises an Experimental Control Module, comprising:
i) a data acquisition parameters control module in operative association with the DAQ;
ii) a MROI control module in operative association with the DAQ;
iii) a custom acquisition programming module in operative association with the DAQ; and,
iv) a camera port control in operative association with the DAQ;

In another non-limiting preferred embodiment, there is provided an automated planner and adaptive sampling system that further comprises a Data Analysis Module (DAQ), comprising:
i) an Image dimension module in operative association with the DAQ;
ii) an image resolution module in operative association with the DAQ;
iii) a color assignment by channel module in operative association with the DAQ
iv) a 3D reconstruction generation module in operative association with the DAQ; and
v) a storage control module in operative association with the DAQ.

In another non-limiting preferred embodiment, there is provided an automated planner and adaptive sampling system that further comprises a BigTiff module in operative association with the DAQ.

In another non-limiting preferred embodiment, there is provided an automated planner and adaptive sampling system that further comprises an Image acquisition software suite module configured to process image data and generate TIFF files from said image data.

In another non-limiting preferred embodiment, there is provided an automated planner and adaptive sampling system wherein the Piezo/Fast Z control module for controlling the position of the mirrors controls the position of the mirrors in three dimensional planes X-Y-Z, wherein the laser is configured as a point spread function (PSF) in a three-dimensional hourglass shape at the specimen, and wherein the Piezo/Fast Z control module is configured to move the point spread function in the Z direction to drive the PSF into the specimen.

In another non-limiting preferred embodiment, there is provided an automated planner and adaptive sampling system wherein the channel digitizer comprises 32 channels, or 16 channels, or 8 channels, or 4 channels, or 2 channels.

In another non-limiting preferred embodiment, there is provided an automated planner and adaptive sampling system that further comprises wherein the full frame scanner module is configured to scan an entire Field of View (FOV) of a specimen and label a detailed high resolution image with multiple possible Region of Interest (ROI) targets within the FOV.

In another non-limiting preferred embodiment, there is provided an automated planner and adaptive sampling system that further comprises wherein the segmentation module is configured to screen the possible ROI targets using an automated segmentation module to locate and confirm targets within the FOV, and to save an X-Y-Z coordinate for each confirmed ROI target.

In another non-limiting preferred embodiment, there is provided an automated planner and adaptive sampling system that further comprises wherein the acquisition planner module is configured to analyze the X-Y-Z coordinates for each confirmed ROI target, and generate an optimized RGG mirror scanning path for the laser to intersect each ROI target and each confirmed ROI target.

In another non-limiting preferred embodiment, there is provided an automated planner and adaptive sampling system that further comprises wherein the acquisition fluorescence sampling module is configured to use the optimized RGG mirror scanning path and record a fluorescence signal from each confirmed ROI target in the FOV.

In another non-limiting preferred embodiment, there is provided an automated planner and adaptive sampling system that further comprises wherein the data viewing module is configured to present in real time two views with the graphical user interface, the first view further comprising a plot of intensity over time of the fluorescent signals from each confirmed ROI target, and the second view further comprising a live presentation of the optimized RGG mirror scanning path over time period t with each confirmed ROI target in the FOV colored by an intensity of fluorescence according to the fluorescent signal last measured at a previous time period t−1.

In another non-limiting preferred embodiment, there is provided an automated planner and adaptive sampling system wherein the multi-photon excitation microscope comprises one or more relay lenses in optical communication with the laser.

In another non-limiting preferred embodiment, there is provided an automated planner and adaptive sampling system wherein the Sampling Rate during wide field of view sampling ranges from 80 MHz-10 GHz.

Methods of Use

In another non-limiting preferred embodiment, there is provided a method for adaptive sampling to maintain a high frame rate during wide field of view sampling in a system for multi-photon excitation microscopy, comprising the steps:
(i) performing a full frame scan of an entire Field of View (FOV) of a specimen and labelling a detailed high resolution image with multiple Region of Interest (ROI) targets within the FOV;

(ii) saving an X-Y-Z coordinate for each ROI target;
(iii) analyzing the X-Y-Z coordinates for each ROI target, and generating an optimized RGG mirror scanning path for the laser to intersect each ROI target;
(iv) using the optimized RGG mirror scanning path and recording a fluorescence signal from each ROI target in the FOV;
(v) presenting in real time two views with a graphical user interface, a first view comprises a plot of intensity over time of the fluorescent signals from each ROI target, and a second view comprises a live presentation of the optimized RGG mirror scanning path over time period t with each ROI target in the FOV colored by an intensity of fluorescence according to the fluorescent signal last measured at a previous time period t−1;
(vi) wherein the multi-photon excitation microscope for multi-region of interest (MROI) imaging of intact cellular tissue comprises:
   (a) a laser configured for multi-photon laser microscopy;
   (b) a Pockels cell operatively associated with the laser to control laser power;
   (c) one or more focusing lenses in optical communication with the laser;
   (d) a compact scanner assembly in optical communication with the laser;
   (e) one or more dichroic mirrors in optical communication with the laser;
   (f) one or more objective lenses in optical communication with the laser;
   (g) one or more photomultiplier tubes in optical communication with the FOV;
   (h) a computer comprising one or more processors, memory, storage memory, interfaces, controllers, and input devices for operating the multi-photon excitation microscope, said computer having a display for receiving the graphical user interface; wherein the modules comprise computer program instructions executable by the one or more processors.

In another non-limiting preferred embodiment, there is provided a method wherein the Frame Rate is at least 80 Hz, or the Frame Rate is at least 100 Hz, or the Frame Rate is at least 200 Hz, or the Frame Rate is at least 500 Hz, or the Frame Rate is at least 1000 Hz, or the Frame Rate is at least 1500 Hz, or the Frame Rate is 2000 Hz, or the Frame Rate ranges from 60 Hz-200 Hz, or the Frame Rate ranges from 100 Hz-200 Hz, or the Frame Rate ranges from 100 Hz-500 Hz, or the Frame Rate ranges from 200 Hz-500 Hz, or the Frame Rate ranges from 200 Hz-1000 Hz, or the Frame Rate ranges from 100 Hz-2000 Hz, or the Frame Rate ranges from 200 Hz-2000 Hz, or the Frame Rate ranges from 500 Hz-2000 Hz, or the Frame Rate ranges from 500 Hz-1200 Hz, or the Frame Rate ranges from 500 Hz-1500 Hz, or the Frame Rate ranges from 500 Hz-2000 Hz.

In another non-limiting preferred embodiment, there is provided a method that further comprises the step of switching from line scanning to frame scanning of a region of the FOV when the fluorescence signal exceeds a pre-set threshold.

In another non-limiting preferred embodiment, there is provided a method that further comprises the step of providing a path correction input to change the coordinates of one or more ROI targets within the optimized mirror scanning path.

In another non-limiting preferred embodiment, there is provided a method that further comprises the step of automatically calibrating a scanning path by generating and saving coordinates of an actual mirror scanning path and comparing the coordinates of the actual mirror scanning path to the coordinates of the optimized mirror scanning path while a scan is in progress, and adjusting the coordinates of the actual mirror scanning path to match the coordinates of the optimized mirror scanning path.

In another non-limiting preferred embodiment, there is provided a method that further comprises the step of automatically calibrating a scanning path by generating and saving coordinates of an actual mirror scanning path and comparing the coordinates of the actual mirror scanning path to the coordinates of an updated optimized mirror scanning path while a scan is in progress, and re-scanning an entire Field of View (FOV) of a specimen, re-labelling a detailed high resolution image with multiple Region of Interest (ROI) targets within the FOV, re-saving an X-Y-Z coordinate for each ROI target, re-analyzing the X-Y-Z coordinates for each ROI target, and generating an updated optimized mirror scanning path for the laser to intersect each ROI target, and adjusting the coordinates of the actual mirror scanning path to match the coordinates of the updated optimized mirror scanning path.

In another non-limiting preferred embodiment, there is provided a method, that further comprises the steps of generating and saving scanner variables while a scan is in progress, said scanner variables comprising scanner motion and scanner orientation for each scanner for each ROI target within a FOV, said Scanner Status Module configured to generate a Scanner Status Report output to the graphical user interface.

In another non-limiting preferred embodiment, there is provided a method that further comprises the steps of generating and saving Sampling Variables selected from vertical resolution, horizontal resolution, frame rate, ROI threshold, and laser power, and adjusting the optimized mirror scanning path for each ROI target within a FOV based on user-selected priority settings of the Sampling Variables, and generating a Variable Priority Status Report output to the graphical user interface.

In another non-limiting preferred embodiment, there is provided a method that further comprises the steps of triggering an automated threshold trigger by adding coordinates of one or more ROI targets within the optimized mirror scanning path in response to a triggering event, and generating and saving a series of image Frames in response to the triggering event.

In another non-limiting preferred embodiment, there is provided a method that further comprises the steps of labelling Possible Targets within the FOV, and labelling and storing the possible targets as a Region of Interest (ROI).

In another non-limiting preferred embodiment, there is provided a method that further comprises the step of screening the ROIs using an automated segmentation module to locate and confirm possible ROI targets within the FOV before saving an X-Y-Z coordinate for each confirmed ROI target.

In another non-limiting preferred embodiment, there is provided a method that further comprises the steps of analyzing the X-Y-Z coordinates for each of the confirmed ROI targets using an acquisition planner, and generating an optimized RGG mirror scanning path for the laser to intersect each ROI target and each confirmed ROI target.

In another non-limiting preferred embodiment, there is provided a method that further comprises the step of using the optimized mirror scanning path and recording a fluorescence signal from each confirmed ROI target in the FOV.

In another non-limiting preferred embodiment, there is provided a method that further comprises a first view that includes a plot of intensity over time of the fluorescent signals from each confirmed ROI target, and a second view that includes a live presentation of the optimized mirror scanning path over time period t with each confirmed ROI target in the FOV colored by an intensity of fluorescence according to the fluorescent signal last measured at a previous time period t−1.

In another non-limiting preferred embodiment, the method uses a two-photon excitation microscope. In another non-limiting preferred embodiment, the method uses a three-photon excitation microscope.

In a non-limiting preferred embodiment, the method uses a compact scanner assembly that comprises a GG scanner assembly, an RG scanner assembly, an RGG scanner assembly, and RGGG scanner assembly, an RGGGG scanner assembly, or a MEMS mirror scanner assembly.

In a non-limiting preferred embodiment, the method uses a compact scanner assembly that comprises a resonant scanner (R) driven at a resonant frequency selected from 8 KHz, 12 KHz, and 16 KHz, a first galvanometer scanner (G1), and a second galvanometer scanner (G2).

In another non-limiting preferred embodiment, the method uses a multi-photon excitation microscope that comprises one or more relay lenses in optical communication with the laser.

In another non-limiting preferred embodiment, the method uses a Sampling Rate during wide field of view sampling ranges from 80 MHz-10 GHz.

BRIEF DESCRIPTION OF THE FIGURES

FIG. 3 also shows additional method steps of the invention including using the optimized path to make real-time adjustments or calibrations in the actual path of the laser during scanning, recording fluorescence signals, and presenting views in a graphical user interface displayed to a user.

FIG. 7 shows a pulsed IR laser, a scanning mirror, a first dichroic mirror, an objective lens, a specimen having fluorophores at the focal plane, a second dichroic mirror, and two photodetectors, a first photodetector configured to detect a first wavelength, a second photodetector configured to detect a second wavelength.

FIG. 8 shows a pulsed IR laser, an RGG scanning mirror assembly, a first dichroic mirror, an objective lens, a specimen having fluorophores at the focal plane, a second dichroic mirror, and two photodetectors, a first photodetector configured to detect a first wavelength, a second photodetector configured to detect a second wavelength.

FIG. 9 also shows optional Path Adjustment Module, optional Automated Calibration Module, optional Scanner Status Module, and optional Variable Priority Module.

FIG. 10 also shows optional method steps of the invention to vary the signal parameters to include possible ROI targets within a FOV, and to screen the possible ROI targets to include confirmed ROI targets.

DETAILED DESCRIPTION OF THE INVENTION

Figure 1:
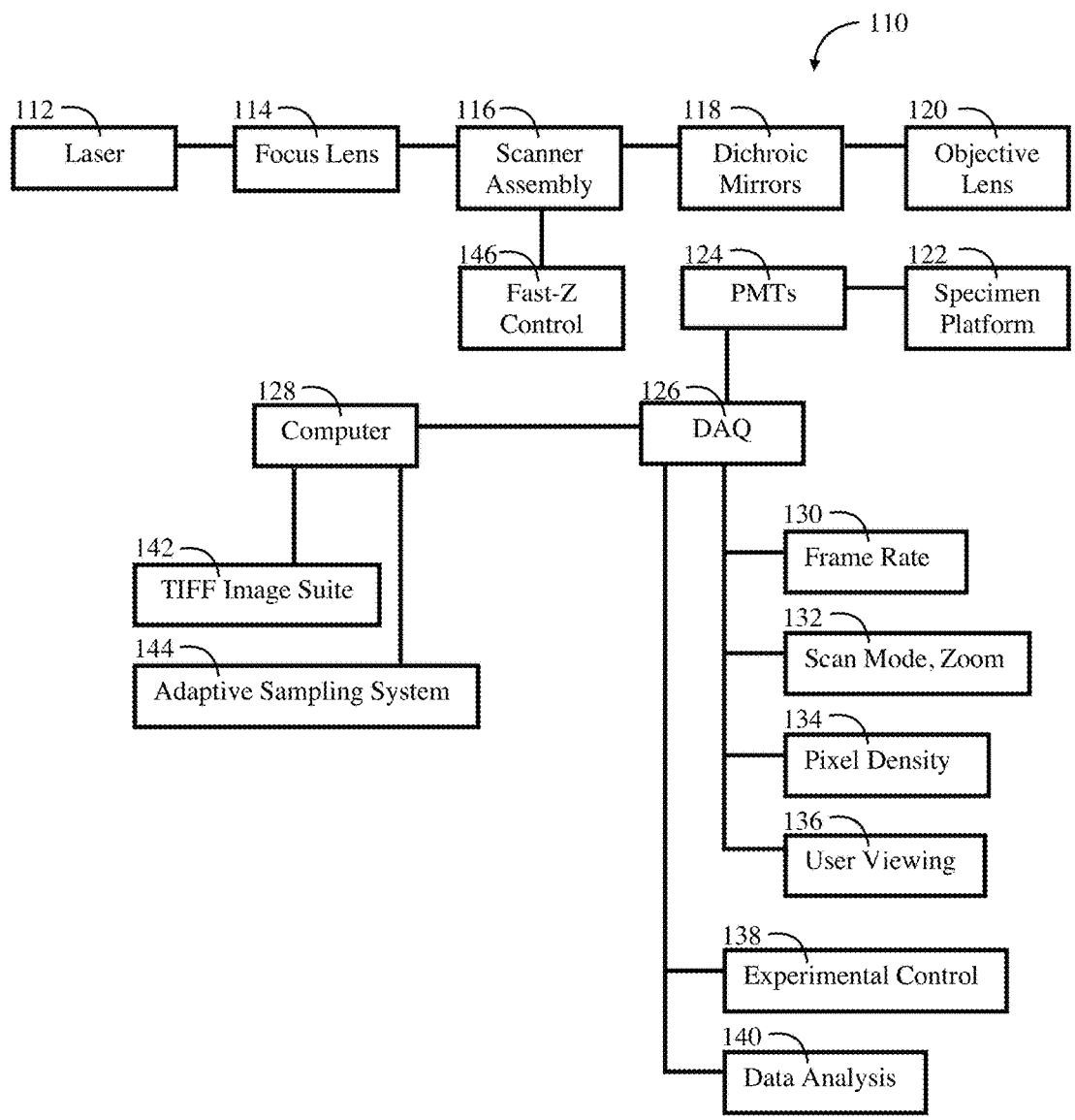
FIG. 1 is a schematic representation of one preferred embodiment of the adaptive sampling system of the present invention and shows the laser assembly, followed by a combination of focusing lenses, scanner assembly, dichroic mirrors, objective lens, photomultiplier tube(s), and electronics including a computer for processing and controlling various modules including a Fast Z piezo Control module, Data Acquisition module(s), Experimental Control module, data Analysis module, Imaging Suite, and Adaptive Sampling Module.

The invention relates to multi-photon excitation microscopy, and in particular to a planner and calibration module for a three mirror system configured to maintain a high frame rate during wide field of view sampling.

While a large FOV multi-photon laser scanning microscope offers an extraordinary field-of-view size, it also presents a unique problem for how to find the ROIs where the interesting activity is occurring. This invention for adaptive sampling is one approach to solving that problem. As stated, the first step in the process would be to do full frame scanning of the entire FOV to provide a detailed high resolution image with which to identify all cells as possible ROIs. This image will then be passed through an automated segmentation algorithm to locate all cells with the FOV. The coordinates of all cells are then passed to an acquisition planner that will determine an optimized scanning path that will intersect every cell. An acquisition can then be initiated using this path to sample the fluorescence across every cell in the FOV.

Frame Scanning Vs Line Scanning

This invention provides line scanning that has the advantage of being able to sample across the entire FOV while still maintaining high frame rate. The data is presented in real time to the researcher in two views. One is an intensity vs time plot of every cell or of groups of cells averaged together. The second view is a live presentation of the scan path with each point along the path colored by the fluorescence intensity last measured at that point. When activity within a certain region of the FOV becomes particularly high, the software can rapidly switch to frame scanning of this region in order to provide the researcher with a better picture of what is happening in this region.

Hardware

The technology relates to a compact laser scanning system. The technique involves using two or sometimes three galvo-mirrors and one resonant scanning mirror in a specific configuration to solve mapping errors and increase the view angle, e.g. to 20 degrees. In one preferred embodiment, the system comprises an IC/CPU motherboard card with a PCI express slot/bus connected to an FPGA A-D converter, the IC card connected to a GPU card, with hardware control connected to the FPGA converter, and a fast SSD e.g. M2, to handle the massive data stream involved with a real-time processing of imaging data correlated to real-time behavioral data collection.

The use of specialized processing such as the FPGA, GPU, or combination of the two results from the realization that hardware is needed for this invention that has processing power to handle the massive data stream involved with a real-time processing of imaging data correlated to real-time behavioral data collection. It is also contemplated as within the scope of the invention to use an ASIC in place of, or in conjunction with the FPGA.

The invention also contemplates a Data Acquisition Card that has analog inputs, and a field programmable gate array (FPGA) very similar to the National Instruments NI-5170 card (http://sine.ni.com/nips/cds/view/p/lang/en/nid/212659). A novel feature of this card is that it has a mechanism to directly connect the output of this card to shared memory on a graphics card that has a graphics processing unit (GPU). Alternatively, the card may contain its own GPU and shared memory between the FPGA and GPU. In the first implementation, the invention contemplates a way to add an Nvidia Direct GPU Connection. In a preferred embodiment, the connection is usually GPU to RAM to BUS to GPU-RAM. In another preferred embodiment, the Nvidia loads direct to the GPU. It is notable that a SLI connection on the data acquisition card that directly connects to the SLI interface on a graphics card would not be operative. However, in a further preferred embodiment, the GPU and FPGA are on the same card and share memory.

Multi-photon excited fluorescence microscopy uses focused laser beams scanned in a raster pattern to generate images, and has an optical sectioning effect produced as a result of the point spread function: the multi-photon point spread function is typically hourglass-shaped (longer in the Y-Z NOT X-Yx-y plane), or in another preferred embodiment, ellipsoidal shaped. It is elongated along the optical axis which is typically assigned as the z axis.

The concept of multi-photon excitation is based on the idea that two, or three, photons of comparably lower energy than needed for one photon excitation can also excite a fluorophore in one quantum event. Each photon carries approximately half, or ⅓, the energy necessary to excite the molecule. An excitation results in the subsequent emission of a fluorescence photon, typically at a higher energy than either of the two, or three, excitatory photons. The probability of the near-simultaneous absorption of multiple photons is extremely low. Therefore, a high flux of excitation photons is typically required, usually from a femtosecond laser. The purpose of employing the multi-photon effect is that the axial spread of the point spread function is substantially lower than for single-photon excitation. As a result, the resolution along the z dimension is improved, allowing for thin optical sections to be imaged. Longer wavelength, lower energy (typically infrared) excitation lasers of multi-photon microscopes are well-suited to use in imaging live cells as longer wavelengths penetrate deeper into the tissue and have less scattering. They also cause less damage than short-wavelength lasers typically used for single-photon excitation, so cells may be observed for longer periods.

The most commonly used fluorophores have excitation spectra in the 400-600 nm range, whereas the laser used to excite the two-photon fluorescence lies in the ~800-1200 nm (infrared) range. If the fluorophore absorbs two infrared photons simultaneously, it will absorb enough energy to be raised into the excited state. The fluorophore will then emit a single photon with a wavelength that depends on the type of fluorophore used (typically in the visible spectrum). Because two photons are absorbed during the excitation of the fluorophore, the probability for fluorescent emission from the fluorophores increases quadratically with the excitation intensity. Therefore, much more two-photon fluorescence is generated where the laser beam is tightly focused than where it is more diffuse. Effectively, excitation is restricted to the tiny focal volume (~1 femtoliter), resulting in a high degree of rejection of out-of-focus objects. This localization of excitation is the key advantage compared to single-photon excitation microscopes, which need to employ additional elements such as pinholes to reject out-of-focus fluorescence. In multi-photon fluorescence, a laser delivers sufficient excitation energy to a fluorophore to cause it to absorb multiple photons, and emit a single detectable photon. For example, a three photon system would use 1500 nm laser applied to a 500 nm fluorophore. In another example, a two-photon system would use 1000 nm laser applied to a 500 nm fluorophore.

The fluorescence from the sample is then collected by a high-sensitivity detector, such as a photomultiplier tube. This observed light intensity becomes one pixel in the eventual image; the focal point is scanned throughout a desired region of the sample to form all the pixels of the image. The scan head is composed of multiple mirrors, the angles of which can be rapidly altered with a galvanometer.

Scanner Embodiments

The invention contemplates a wide variety of scanning systems including linear (galvo/galvo, GG), resonant/galvo (RG) systems, resonant/galvo/galvo (RGG) systems, resonant/galvo/galvo/galvo (RGGG) systems, resonant/galvo/galvo/galvo/galvo (RGGGG) systems, and MEMS mirror systems. Resonant scanning with multiple regions of interest (MROI) is supported for all listed systems. Parallel scanning systems are supported to provide simultaneous imaging and photostimulation.

In a non-limiting preferred embodiment, the Galvo-Resonant Scan Head has three scan mirrors—RGG. The resonant scanning mirror, X, is an 8 KHz resonant scanner mirror, or is a 12 KHz resonant scanning mirror, or is a 16 KHz resonant scanning mirror. When considering the path of the laser from the source to the sample, in one preferred embodiment, an RGG embodiment is provided wherein the resonant mirror R=X is first, followed by the first galvanometer scanning mirror, G1=X also in the X axis, and the second galvanometer scanning mirror, G2=Y in the Y axis, with a FastZ device added for the Z-axis or Z dimension. In another preferred embodiment, an GRG embodiment is provided wherein the first galvanometer scanning mirror G1=X axis, followed by the resonant mirror R=X axis is second, followed by the second galvanometer scanning mirror G2=Y axis, with a FastZ device added for the Z-axis or Z dimension. In yet another preferred embodiment, an GGR embodiment is provided wherein the first galvanometer scanning mirror G1=X axis, followed by the second galvanometer scanning mirror G2=Y axis, followed by the resonant mirror R=X axis, with a FastZ device added for the Z-axis or Z dimension. In yet a further aspect, an RGGG embodiment is provided wherein the resonant mirror R=X axis is first, followed by the first galvanometer scanning mirror, G1=X axis, followed by the second galvanometer scanning mirror, G2=X axis, followed by the third galvanometer scanning mirror G3=Y axis, with a FastZ device added for the Z-axis or Z dimension.

A MEMS scanner assembly refers to a MEMS (Micro Electro Mechanical System) mirror that is a tiny solid-state mirror (mirror on a chip) actuated by micro-size motors in one or two dimensions. A laser beam pointed at the mirror is precisely deflected and steered by the scanning mirror to reach a target point at a specific time. MEMS laser scanning mirrors may obtained from, e.g. Maradin Corp.

Within the scan path assembly, the NIR laser is fed through a series of scanning mirrors, focusing lenses, optional relay lenses, Objective lens(es), and Dichroic mirrors.

Frames, Pixels, and Programs

Since the laser and scanner assembly is capable of scanning across a samples FOV, the rate that the laser and scanner assembly completes one frame is called the Frame rate and is measured in frames per second. The frame rate also depends on the number of pixels that are being generated within a certain space. For instance, a typical frame rate includes 30 FPS at 512×512 pixels, or 400 FPS at 512×32 pixels, or 2 FPS at 4096×4096 pixels. Note that the frame rate decreases as the number of pixels per frame, pixel density, increases.

The two photon laser scanning microscope may also scan in programmed geometries. For example, the invention includes Scan modes such as line scanning, square scanning, and rectangular scanning.

Scan zooming is also an aspect of the present invention. Zoom powers of up to 100× are contemplated depending on the optics that are chosen. In an alternate embodiment, Zoom powers of up to 100×, but also from 1×-36× are contemplated depending on the optics that are chosen.

One of the main advantages of multi-photon laser scanning microscopy is the ability to provide high scan resolution. The invention includes optimized data acquisition algorithms that achieve maximum pixel density of at least 2048×2048 bi-directional and 4096×4096 unidirectional.

The laser wavelength also matters. If the laser is too powerful, or a wavelength that damages tissue is chosen, the two photon laser microscope can result in tissue bleaching and tissue damage. The present invention is directed to near infrared lasers to avoid such problems.

Group Delay Dispersion

The optical lenses and/or the scanning mirrors ideally have a low group delay dispersion (GDD). Dispersion of the laser at the lenses or mirrors requires longer pulses, adversely affecting imaging. In order to have the shortest pulse at the sample, the lenses and scanning mirrors need to have the lowest GDD possible. In preferred embodiments, the GDD is <100 $fs^2$. In another preferred embodiment, the GDD is <50 $fs^2$. In another preferred embodiment, the GDD is <30 $fs^2$. The use of mirrors having high reflectance coatings (R>99%) in the critical wavelength range and at the angle of incidence that is required (up to AOI=45) allows for the use of extremely short pulses. Exemplary mirrors are available from Cambridge Technology.

Adjunct technologies, such as dispersion compensators, and relay lenses, available from Thor Labs, are sometimes used in conjunction with scanning mirrors, to provide an even lower GDD.

Dichroic Mirrors

The dichroic mirrors are coated to be reflective to certain wavelengths and transmissive to other wavelengths. This allows the laser to travel through one side of a dichroic mirror to access a sample or specimen, and the emitted fluorescent signal from the sample to reflect off the dichroic mirror and be re-directed to adjacent or orthogonal light detectors. An example of one type of dichroic mirror has a reflectivity <680 nm, and transmissiveness of 680-1400 nm. Another example of a dichroic mirror has a reflectivity of <760 nm, and transmissiveness of 760-1100 nm. Dichroic mirrors and matching emission or excitation filter sets are available from Cambridge Technology.

Filters

At certain points within the laser path, it is contemplated that blocking filters are used to prevent backscatter illumination into the sample. In a preferred embodiment, an NIR blocking filter is positioned (in the light path) between the first and the second dichroic mirrors. Emission filters may also be necessary and are contemplated as within the scope of the invention. In a preferred embodiment, an emission filter is positioned in the light path just prior to each of the GaAsP PMTs.

Photomultiplier Tubes

The devices that detect the illumination are Photomultiplier Tube(s). The present invention contemplates the use of two non-descanned PMTs. PMTs are often made and defined according to the rare compounds that are used to manufacture them, such as Gallium-Arsenic-Phosphorous GaAsP. PMTs also usually require a preamplifier such as a transimpedance amplifier to operate correctly.

Computers

For image processing and other computational needs, the invention requires a Computer that has a CPU 64-bit Quad core>3.5 ghZ 16 G RAM, a FPGA, a GPU, appropriate interfaces, buses, and drivers, RAM memory >8 GB, at least 2 PCIe slots and preferably 4, and a hard drive storage such as SSD or HD>500 GB.

Example—Computer 1

In one non-limiting preferred embodiment, the computer comprises an i5 3.5 GHz CPU on an Asus or Gigabyte Z97 or H97 mini-ITX motherboard, 8 Gb RAM or more, a 500 GB SSD for the OS, a 2 TB hard drive for storage, a 550-watt power supply, and a housing.

Example—Computer 2

In another non-limiting preferred embodiment, the computer comprises an i7-4790K 4.0 GHz CPU on an Asus or Gigabyte socket 1150 motherboard, 16 Gb RAM or more, a 500 GB SSD for the OS with >500 MB/sec sequential read/write, two 2 TB hard drives in RAID 0 for storage with >300 MB/sec sequential write, a 650-watt power supply, and a housing.

Example—Computer 3

In another non-limiting preferred embodiment, the computer comprises an i7-6850K 6-core 3.6 GHz CPU on an Asus socket 2011-v3 motherboard, 16 Gb DDR4 RAM or more, a 500 GB SSD for the OS with >500 MB/sec sequential read/write, two 2 TB hard drives in RAID 0 for storage with >300 MB/sec sequential write, a 750-watt power supply, a GTX1060 Graphics card, and a housing.

In one preferred embodiment, the PCIe's are programmed using a software tool such as Verilog.

The term "Field Programmable Gate Array" (FPGA) refers to an integrated circuit that is custom configured using hardware description language. FPGAs contain an array of programmable logic blocks, and a hierarchy of reconfigurable interconnects that allow the blocks to be "wired together", like many logic gates that can be inter-wired in different configurations. Logic blocks can be configured to perform complex combinational functions, or merely simple logic gates like AND and XOR. In most FPGAs, logic blocks also include memory elements, which may be simple flip-flops or more complete blocks of memory.

In one preferred embodiment, the software tool, LabView is used to program the FPGA. the use of FPGAs in the present invention provide data reduction by pre-processing in the FPGA. The FPGA can also be used to bin data into pixels in order to free up CPU use, which improves the latency of the system.

The term "Application Specific Integrated Circuit" (ASIC) refers to an integrated circuit that is pre-configured in its logic architecture to perform a specific function, and is not reconfigurable.

The term "Digital Signal Processing" and/or "Digital Signal Processor" (DSP) refers to software programming instructions executed on a specialized microprocessor that is optimized for performing software programming instructions used to execute digital signal processing algorithms. Non-limiting examples of the functions of such algorithms include converting analog to digital, performing required mathematical processes, and detecting and correcting digital electronic transmissions. Specific DSP tools include MATLAB® and SIMULINK® for providing algorithms, applications and scopes for designing, simulating and analyzing signal processing for the invention, including designing and implementing any embedded code, software defined logic architectures, FIR, IIR, multirate, multistage and adaptive filters, streaming signals from variables, data files, and network devices. Software, like MATLAB® etc., is contemplated for use as either or both a DSP software hardware-substitute of FPGAs and/or ASICs, adjuncts for FPGAs and ASICs, and/or control software for FPGAs and ASICs.

FPGAs, ASICs, and DSPs are all contemplated as within the scope of the invention.

Electronic Control Unit

Connected to the laser assembly and the computer is an electronic control unit. The ECU preferably includes a controller such as a National Instrument integrated controller, e.g. NI PXIe-1073, a data module such as the Data Acquisition (DAQ) module, e.g. NI PXIe-6341, a Digitizer, 2 or 4 channel, e.g. NI 5732 or 5734, a FPGA Module, e.g. NI PXIe7961R, or 7975R, and a Pockels control module.

Piezoactuators

Also, the invention may include a Piezo/Fast Z control for volume imaging. An example of the Piezo hardware, is that provided by Physik Instrumente, piezosystem Jena, or nPoint. The assembly may also include staging hardware. In preferred embodiments, the piezo hardware comprises piezoactuators selected from the group consisting of: a multilayer stack piezoactuator, a monolithic piezoactuator, a tube piezoactuator, a multilayer ring piezoactuator, a bimorph piezoactuator, and a hybrid piezoactuator.

In a preferred embodiment, the piezoactuator is a piezotube. Piezotubes are made from a monolithic ceramic; they are metalized on the inner and outer surface. Normally, the inner surface is contacted to the positive voltage. If an electric field is applied to the tube actuator, a contraction in the direction of the cylinder's axis, as well as a contraction in the cylinder's diameter, results in a downward motion. If the outer electrodes are divided, the tube can work as a bimorph element. In this way, it is possible to reach a larger sideways motion. Piezotubes are preferred for mirror mounts, inchworm motors, AFM (atomic force microscopes) and STM microscopy. In one example of a piezotube actuator with a diameter of 10 mm, a wall thickness of 1 mm and a length of 20 mm. The maximum operating voltage is 1000 V. So, the applied field strength is 1 kV/mm. The transversal piezoelectrical effect shows a relative contraction of approximately 0.05%. For the length of 20 mm, one will get an axial contraction of 10 μm. Simultaneously the circumference of 31.44 mm will be shorter by 15 μm. This is related to a radial contraction of 4.7 μm.

In another preferred embodiment, the piezoactuator is a ring piezoactuator. Ring actuators are built similarly to multi layer stack actuators, but with a central axial aperture, making it possible to perform radial movement for small components. This type of actuator is preferred in the field of beam manipulation and laser resonators. The mechanically prestressed versions of these actuators can be used dynamically.

In another preferred embodiment, the piezoactuator is a piezostack. Piezostacks consist of a large number of stacked ceramic discs. The electrodes are arranged on both sides of the ceramic discs and are connected in a parallel line. Piezostacks are also called actuators, piezoelectrical actuators or piezoelectrical translators. In one example, a stack actuator may consist of 20 ceramic plates, and with a thickness of one plate about 0.5 mm, the total length of the actuator is 10 mm. The actuator will reach a maximum expansion of approximately 10 µm for a voltage of 1000 V (high voltage actuator). For plates with a smaller thickness the maximum voltage will be less. Modern multi-layer actuators consist of ceramic laminates with a thickness of typically 100 µm and works at voltages typically 130 V high. In one example, a multi-layer stack actuator with a total length of 10 mm may consist of 100 disks with a thickness of 100 µm. The stack will reach nearly the same expansion of 10 µm with a voltage of 130 V.

In another preferred embodiment, the piezoactuator is a monolithic actuator. This means, the material is sheet ceramic that is laminated with electrode material. In this way, the full monolithic actuator will be made as one system, and the actuator will have the equivalent parameters (for example a high stiffness) of a solid ceramic material.

In another preferred embodiment, the piezoactuator is a bimorph. The bimorph piezoactuator is made from two thin piezoelectrical ceramic plates mounted on both sides with a thin substrate. The principle is similar to thermo bimetal circuits, where, by applying opposite field strength to the ceramic plates, one plate shows a contraction, the other will expand. The result is bending in the order of sub-mm up to several mm. Bimorph elements use the transversal piezoelectrical effect. Piezoelectric bimorph elements may have a resonant frequency of several 100 Hz. Bimorph piezos may consist of a Serial Bimorph, or a Parallel Bimorph. In a Serial Bimorph, both piezoelectrical plates are polarized in opposite directions. A voltage is applied to the electrodes on the ceramic plates on the outside. If a voltage is applied and the plate shows a contraction, the other will show an expansion. In a Parallel Bimorph piezoactuator, a metal plate middle electrode is between the two ceramic plates. The polarization of both ceramic plates is in the same direction. The bending of this bimorph will be reached by applying opposite voltages to the electrodes. Because of the metal plate in the middle, these bimorph elements have a higher stiffness.

In another preferred embodiment, the piezoactuator is a Hybrid. Hybrid Piezoactuators combine elements from one or more other types of piezoactuator designs into a single unit. In one example, a Hybrid Piezo contains elements, such as in a MINITRITOR 38 from piezosystem jena corp., that generates a rectangular motion of 38 µm in x, y and z direction. By using integrated solid state hinges with parallelogram design, this Hybrid Piezo provides parallel motion without any mechanical play. For that example, the dimensions are 19 mm×19 mm×16 mm. In another example, a Hybrid Piezo comprises a PX 400. This piezoactuator gives a motion of 400 µm; the dimensions are 52 mm×48 mm×20 mm. This element is also suited for dynamical motion.

Piezo Alternatives—Other Focusing Technologies

In another preferred embodiment, the use of a piezo to move the scanning mirrors can be replaced or supplemented by using other focusing technologies. Focusing technologies within the scope of the invention include electronically tunable lenses, remote focusing, TAG lenses, and deformable mirrors. Electronically tunable lenses, such as those by Optotune Corporation, are able to adjust a lens in the Z direction, i.e. adjust the focal length, adjust the PSF, are able to do so faster than piezo technology, and do not require the system equipment level movements that can be associated with piezo use. Remote focusing is another focusing technology contemplated as within the scope of the invention and moves mirror(s) by using a magnet to control a back and forth motion to change the focal length. A TAG lens is another focusing technology contemplated as within the scope of the invention and uses lenses that vibrate in the Z direction to change the focal length. Deformable mirrors are another focusing technology contemplated as within the scope of the invention and using voltage deformable reflective polymer mirrors to change the focal length, such as those available from Revibro Optics.

Lasers

In one preferred embodiment, the laser is a laser operating in the Near Infrared (NIR) wavelength range. In a preferred embodiment, the femtosecond laser may be a NIR laser with wavelength range 680-1400 nm. The laser may be tunable or may have a preset, fixed wavelength. In another preferred embodiment, the femtosecond laser may be a NIR laser with wavelength range 760-1100 nm. In a non-limiting preferred embodiment, the laser is a Ti-Sapphire oscillator, that has a femtosecond pulse width. Exemplary lasers include lasers from Spectra-Physics including InSight DS+, Mai Tai DeepSee, Mai Tai, Inspire, femtoTrain, and HighQ-2. http://www.spectra-physics.com. Dichroic mirrors and matching emission/excitation filters allow for a chosen cutoff wavelength, e.g. 650 nm, with a reflection band (or transmission band) below the cutoff, e.g. 400-630 nm, and a transmission band (or reflection band) above the cutoff, e.g. 685-1600 nm. Also contemplated as within the scope of the invention is the use of green light lasers with green light excitable fluorophores (GFP), IR light lasers with IR light excitable fluorophores, Far IR light lasers with FIR light excitable fluorophores, and blue light lasers with blue light excitable fluorophores (BFP). Three-photon fluorophores, such as the calmodulin sensing GCAM-6, works with a 1300 nm laser to excite the 433 nm fluorophore, to generate an emission photon.

Objective

The Objective lens preferably has a pupil diameter of about 10-30 mm. In one preferred embodiment, the Objective lens preferably has a pupil diameter of about 20 mm. In one preferred embodiment, the objective is comprised of a plurality of stacked lenses.

Software Modules

Various modules are included in the invention and which are necessarily in operative association with the assembly hardware. Modules comprise the logic and the computer program instructions necessary to perform the stated function. These functions as stated are non-limiting and the modules will necessarily be tailored to have additional features, menus, interfaces, etc. The module computer program instructions are executable by a processor within the DAQ, the CPU or GPU.

An Equipment Control Module comprises a laser power control module used in conjunction with a Pockels cell to control laser power, a laser wavelength output control, a resonant mirror control, a galvanometer 1 control, a galvanometer 2 control, a frame rate control module, a scan mode control module, a scan zoom control module, a data acquisition pixel density control module, a light path adjustment module for dichroic mirrors, and a user viewing module. A shutter control module is also contemplated for use with shutters that are used to protect the PMTs or block the lasers in a light path. Additionally, the invention may include modules for integration with electrophysiology suites using master or slave TTL signals.

An Experimental Control Module includes a data acquisition parameters control module, a MROI control module, a custom acquisition programming module, and a camera port control.

A Data Analysis Module includes an Image dimension module, an image resolution module, a color assignment by channel module, a 3D reconstruction generation module, a storage control, and a BigTiff module.

It is contemplated that the computer will possess an Image acquisition software suite, for receiving, generating, manipulating, saving, storing, and transmitting the TIFF and AVI files that a generated by the scanner.

Field of View (FOV) is defined as the diameter of the view field in an optical microscope and is also termed the field number. The field number represents the diameter of the field measured in millimeters at the intermediate image plane. An example is:
FOV=5 mm,
16 mm diagonal square at the intermediate image plane,
700 um×700 um at sample with Nikon 16× objective lens.
ScanImage Tiff File Format, aka Big Tiffs aka Extended Tiff Files Since the invention generates large amounts of scanned data that needs to be captured, manipulated, stored, transmitted, and so forth, an important feature is the ability to manage large files, e.g. >4 GB tiff files. ScanImage File Format Tiffs (SIFF Tiffs) extend beyond standard Tiffs to encode video data and metadata.

For the SIFF Tiff feature, Frame Specific Data is defined as Data recorded in a Tiff that is specific to a Frame, such as timestamps and I2C data. This data is stored with each frame. The abbreviation IFD is Tiff Standard terminology, and stands for Image File Directory. The term Non-Varying Frame Data refers to microscope configuration that pertains to all frames in a Tiff file. This data is stored once in the Tiff file following the Tiff Header section. The term ROI Group Data refers to Defined Regions of Interest. This data is stored once in the Tiff file following the Non-Varying Frame Data.

The SIFF Tiff format provides the ability to decipher what the specific bytes means within a captured tiff files. A hex editor is used to display the bytes as they appear in the Tiff file. Byte swapping needs to occur to decipher Tiff information.

In SIFF, the Tiff Header Section contains Tiff Header information as defined in the SIFF Tiff Specification.

In SIFF, the first 2 bytes of the Tiff file defines whether Little Endian or Big Endian byte order is used.

A Magic Number is a 4-byte unsigned number that identifies the file as a Tiff file created by the software used and is currently set to the decimal value, 117637889. This value is placed in the first four bytes of the Static Metadata section. To obtain this, convert the bytes to obtain the value in the example: 0103 0307→0703 0301. This is the hex value that converts to the decimal number 117637889.

A software Tiff Version Number may be set to 3. This is stored as a 4-byte unsigned number following the Magic Number, starting at byte 4 and continuing through byte 7, of the static metadata section. To obtain this, convert the bytes to obtain the value in the example: 0300 0000→0000 0003. This is the hex value that converts to the decimal number 3.

A Non-Varying Frame Data Length section is a 4-byte unsigned number that contains the size in bytes, including a NULL terminator, of the Non-Varying Frame data. The actual Non-Varying frame data starts at byte 16 from the beginning of the Static Metadata section and is discussed in bullet item (5) Non-Varying Frame Data. To obtain this, convert the bytes to obtain the value in the example: E61F 0000→0000 1FE6. This is the hex value that converts to the decimal number 8166. Thus, the size of the Non-Varying Frame Data is 8166 bytes.

A ROI Group Data Length section is a 4-byte unsigned number that contains the size in bytes, including a NULL terminator of the ROI Group data. The actual ROI Group data starts immediately following the Non-Varying Frame Data and is discussed in bullet item (5) Non-Varying Frame Data. To obtain this, convert the bytes to obtain the value in the example: 9F04 0000→0000 049F. This is the hex value that converts to the decimal number 1183. Thus, the size of the ROI Group Data is 1183 bytes.

A Non-Varying Frame Data section contains the actual, unchanging data (excluding ROI Group data) including a NULL terminator, that pertains to all images in the Tiff file. The Non-Varying frame data starts at byte 16 from the beginning of the Static Metadata section. Each Tiff Frame contains an IFD tag, called the 'Software' tag, that points to the start of the Non-Varying Frame data.

A ROI Group Data section contains the actual ROI Group Data, including a NULL terminator. The ROI Group data starts at byte immediately following the Non-Varying Frame Data. Thus the start of the ROI Group Data can be found at the offset of byte 16 plus the size of the Non-Varying Frame Data from the beginning of the Static Metadata section.

There is one frame section existent per image frame. Each Frame section consists of an IFD (Image File Directory) Header, followed by a section containing supplemental header information and finally the bytes that makeup the actual image.

The IFD Header Section contains all the IFD Tags used in the Tiff file. Each IFD Tag utilized is defined within the Tiff Specification. Each frame in the Tiff file contains the same set of IFD Tags filled with frame specific information. To begin, the IFD Header Section of the first IFD Frame starts at the location indicated in the Tiff Header section. Subsequent IFD Header sections start at the location indicated in the 'Next IFD Header' offset field in the IFD Header.

The number of tags is an unsigned 8-byte number stored at byte zero of the IFD header and contains the number of IFD Tags stored in the IFD Header. Below, the IFD Header starts at hex byte 0000 24AA and continues through hex byte 0000 24B0. To obtain this, convert the bytes to obtain the value in the example: 1200 0000 0000 0000→0000 0000 0000 0012. This is the hex value that converts to the decimal number 18. Thus, there are 18 IFD Tags stored in the IFD Header.

Examples of tags include image width, image length, bits per sample field, compression field, photometric interpretation field, image description field, strip offsets field, orientation field, samples, per pixel field, rows per strip field, strip byte counts field, X resolution field, Y resolution field, planar configuration field, resolution unit field, software package field, artist/ROI group metadata offset, and sample format field.

Additional Definitions

"Acquisition" refers to a finite set of acquired frames (at one or more axial slices) collected "Acquisition Mode" refers to a ScanImage setting that supports three acquisition modes termed FOCUS, GRAB, and LOOP. FOCUS is a control of acquisition parameters, GRAB is a single acquisition and a LOOP consists of multiple acquisitions.

"Beams" refers to a term for output DAQ channels used to control laser power modulation devices, which set laser power and blank laser illumination during non-imaging portions of line/frame/acquisition mode.

"Channel" or "Channels" refers to the number of input DAQ channels connected.

"Configuration (CFG)" refers to the large (nearly complete) set of ScanImage setting values which users can modify to control operation of a subsequently started ScanImage acquisition mode. Can be saved & loaded to/from CFG files.

"FastZ" refers to a colloquial term for control of volume imaging, the collection of live multi-frame (movie) acquisitions spanning multiple axial planes. Volume imaging devices are typically fast axial scanners allowing rapid sweeps or steps of axial position without interrupting lateral scanning. FastZ devices are distinguished from plain stage controllers which can be used. FastZ devices can (and usually do) double as stage controllers as well.

"Imaging System" refers to the type of scanner set that is used to form an image. Currently three types are supported—Resonant (resonant-galvo RG or RGG scanner set) and Linear (galvo-galvo GG scanner set).

"Machine Data File" refers to an M file script parsed on ScanImage startup to specify rig-specific settings, such as the hardware present and connection channels. This must be user created & edited prior to first ScanImage operation.

"ROI" stands for "Region of Interest". "MROI" stands for "Multi Region of Interest". ROI setting is a three-dimensional set of ScanFields at various planes which form a bounding volume of interest to be imaged in Multi-ROI imaging mode.

"ScanField" is a term for the set of scanner zoom, angular shift, rotation, and aspect ratio settings which determined the scanned area relative to the full scanner field-of-view at the current stage controller position.

"Pixel" refers to a single scalar element (PICTure ELement) of a multicomponent digital image representation. A pixel is the smallest point unit of a digitally sampled image, and pixels are arranged in regular and irregular grids.

"Process" means an algorithm, software, subroutine, computer program, or methodology.

"Algorithm" means: sequence of steps using computer software, process, software, subroutine, computer program, or methodology.

"Processor" or "image processor" as used in the following claims includes a computer, multiprocessor, CPU, minicomputer, microprocessor or any machine similar to a computer or processor which is capable of processing algorithms.

"Operations" as used in the following claims includes steps, a series of operations, actions, processes, subprocesses, acts, functions, and/or subroutines.

"Optimize" refers to calculating a two-dimensional X-Y or three-dimensional X-Y-Z path or trajectory for a laser, wherein the path is drawn from individual ROI targets that are selected from a group of ROI targets identified in a Field of View, wherein the path or trajectory is calculated using one or more of the following characteristics:

1. is a shortest path, and/or
2. generates the fastest Frame Rate, and/or
3. results in the least tissue damage, and/or
4. uses the lowest laser power, and/or
5. requires the least scanning mirror movement, and/or
6. requires neuron activation using an optogenetics-based rhodopsin channel.

Referring now to the drawings, FIG. 1 shows a schematic representation of one preferred embodiment of the adaptive sampling system 110 of the present invention and shows the laser assembly 112, followed by a combination of focusing lenses 114, scanner assembly 116, dichroic mirrors 118, objective lens 120, photomultiplier tube(s) 124, and electronics including a computer 128 for processing and controlling various modules including a Fast Z piezo Control module 146, Data Acquisition module(s) (DAQ) 126, Experimental Control module 138, Data Analysis module 140, TIFF Imaging Suite 140, and Adaptive Sampling Module 144. DAQ 126 includes Frame Rate module 130, Scan Mode and Zoom module(s) 132, Pixel Density module 134, and User Viewing module 136.

Figure 2:
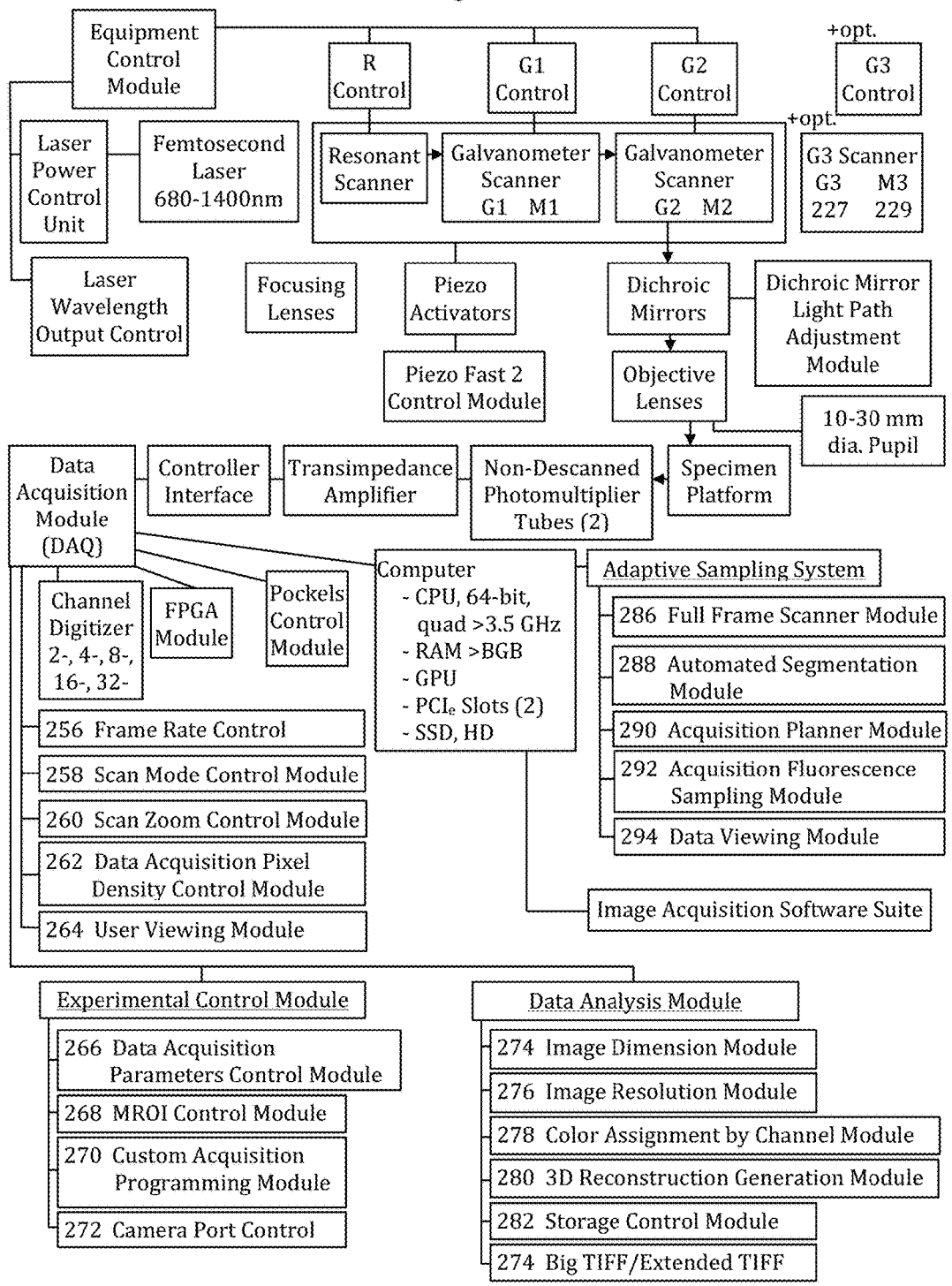
FIG. 2 is a schematic representation of another preferred embodiment of the adaptive sampling system of the present invention and shows the laser assembly, followed by a combination of focusing lenses, exemplary non-limiting RGG(G) scanner assembly, dichroic mirrors, objective lens, optional relay lenses, photomultiplier tube(s), and electronics including a computer for processing and controlling various modules and units including a laser power control, laser wavelength output control, piezo unit, a Fast Z piezo Control module, Equipment Control, Scanner controls, Data Acquisition module(s), Experimental Control module, Dichroic Path Adjustment, Objective Control, PMT control & module, Amplifier control, controller interfaces, Data Analysis module, Channel digitizers & module, FPGA module, Pockels module to control laser power, Frame Rate Control & module, Scan Mode Control & module, Pixel Density Control & module, User Viewer Control & module, Data Analysis control & module, Imaging Suite, and Adaptive Sampling Controls & Module.

FIG. 2 shows a schematic representation of another preferred embodiment of the adaptive sampling system 110 of the present invention and shows the laser assembly 212, followed by a combination of focusing lenses 114, RGG(G) scanner assembly 116, dichroic mirrors 118, objective lens 120, photomultiplier tube(s) 243 and 244, and electronics including a computer 128 for processing and controlling various modules and units.

Laser 212 is a femtosecond laser having a wavelength range specified from 680-1400 nm or 760-1100 nm. The laser photon beam travels through one or more focusing lenses 114. The laser photon beam directed into the RGG scanner assembly 116.

The scanner assembly 116 comprises an RGG architecture with (G1) galvanometer scanner 220 and mirror (m1) 221, (R) Resonant scanner 224, and (G2) galvanometer scanner 226 and (m2) mirror 228. Optional additional galvanometer (G3) 227 and mirror (m3) 229 are contemplated as within the scope of certain embodiments of the invention. Piezo unit 148, and Fast Z piezo Control module 146 operate the motion of the scanning mirrors.

Laser 212 and scanner assembly 116 are controlled by Equipment Control Module 230 (ECM). ECM 230 controls both the laser power control 231, and the laser wavelength output control 233. ECM 230 also controls scanner G1 control 232, R control 234, and scanner G2 control 236.

Within the light path are Dichroic mirrors 118 that are controlled by Dichroic Mirror Light Path Adjustment module 240. Before the light reaches the specimen platform 122, the beam travels through Objective lens 120. Objective lens 120 has a 10-30 m pupil diameter 242 and is operationally controlled by Objective Control 241.

Once the beam has probed the target and has excited the fluorophores, generating an electromagnetically detectable signal, the signal is detected by Photomultiplier tubes 243, 244 (PMTs). PMTs are controlled by PMT control 245 & module 124. The signal is then processed using a transimpedance amplifier 246 before reaching controller interfaces 248, and Data Acquisition module(s) 126 (DAQ).

The DAQ 126 is operationally connected to Experimental Control module 138, Data Analysis module 140, Channel digitizers & module 250, FPGA module 252, Pockels module 254, computer 128, Frame Rate Control & module 256, Scan Mode Control & module 258, Scan Zoom Control and module 260, Data Acquisition Pixel Density Control & module 262, User Viewer Control & module 264.

Experimental Control Module 138 comprises Data Acquisition Parameters Control module 266, MROI control module 268, custom acquisition programming module 270, and camera port control 272.

Data Analysis module 140 comprises image dimension module 274, an image resolution module 276, a color assignment by channel module 278, 3D reconstruction generation module 280 storage control module 282, and Extended Tiff aka BigTiff, aka ScanImageTiff module 284.

Computer 128 includes a 64-bit quad-core 3.5 GHz CPU, a GPU, 8 GB RAM or better, at least two PCIe slots, and HD or SSD storage memory.

TIFF Imaging Suite 142, is an image acquisition software suite to process image data and generate TIFF files.

Adaptive Sampling Controls & Module 144 comprises Full Frame Scanner module 286, Automated Segmentation module 288, Acquisition Planner Module 290 Acquisition Fluorescence Sampling Module 292, and Data Viewing Module 294.

Figure 3:
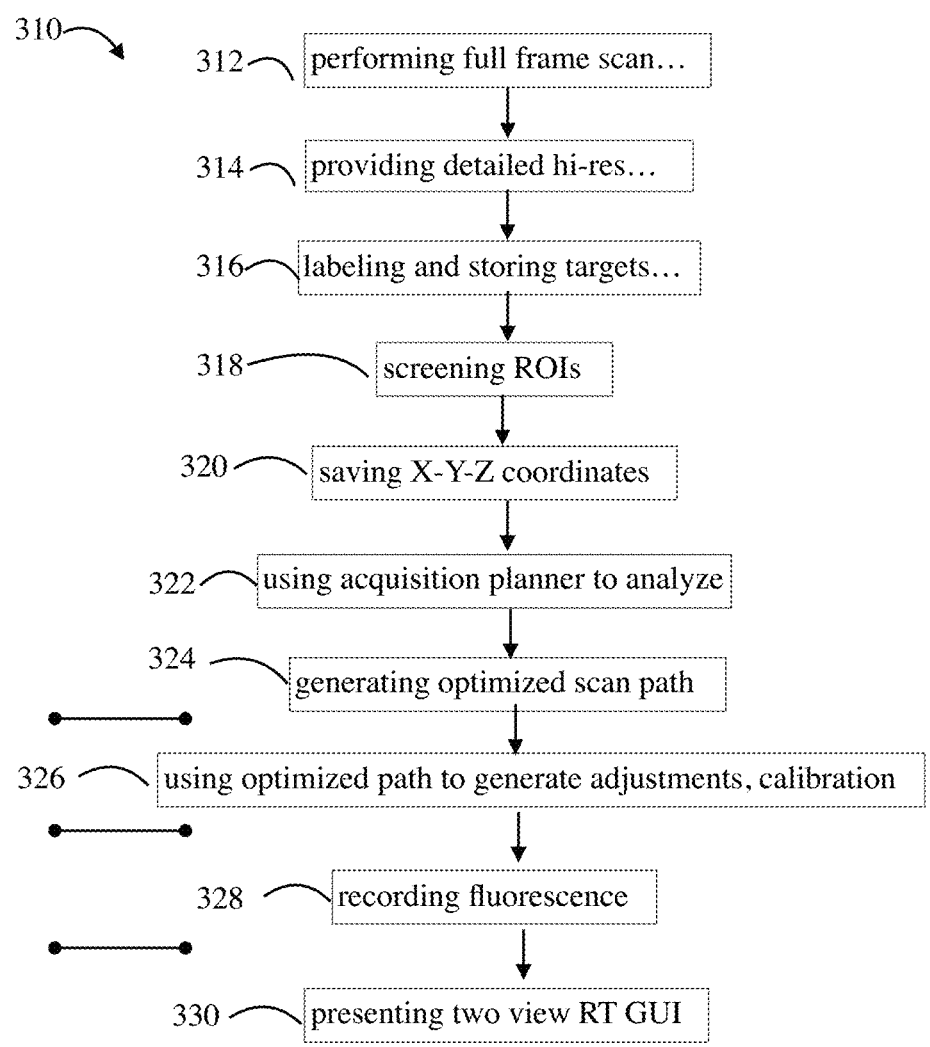
FIG. 3 is a flowchart representation of steps in one preferred method embodiment of the present invention showing scanning, imaging, labelling targets, screening ROIs, saving coordinates, and using a planner to generate an optimized path.

FIG. 3 is a flowchart representation of steps in one preferred method embodiment of the present invention showing the steps comprising Step 312 performing a full frame scan of an entire Field of View (FOV) of a specimen and Step 314 obtaining a detailed high resolution image with multiple Region of Interest (ROI) targets within the FOV. Step 316 Labelling and storing detailed high resolution image with multiple Region of Interest (ROI) targets within the FOV. Step 318 optionally screening the ROIs for targets meeting selection criteria, and Step 320 saving an X-Y-Z coordinate for each ROI target and/or confirmed ROI target. Step 322 comprises analyzing the X-Y-Z coordinates for each ROI target, and Step 324 comprises generating an optimized RGG mirror scanning path for the laser to intersect each ROI target. Once an optimized path is generated, additional steps are contemplated including Step 326 using the optimized RGG mirror scanning path and Step 328 recording a fluorescence signal from each ROI target in the FOV. Additional Step 330 comprises presenting in real time two views with a graphical user interface, a first view comprises a plot of intensity over time of the fluorescent signals from each ROI target, and a second view comprises a live presentation of the optimized RGG mirror scanning path over time period t with each ROI target in the FOV colored by an intensity of fluorescence according to the fluorescent signal last measured at a previous time period t−1. Additionally Step 326 can include using the optimized path to make real-time adjustments or calibrations in the actual path of the laser during scanning, recording fluorescence signals, and presenting views in a graphical user interface displayed to a user.

Figure 4:
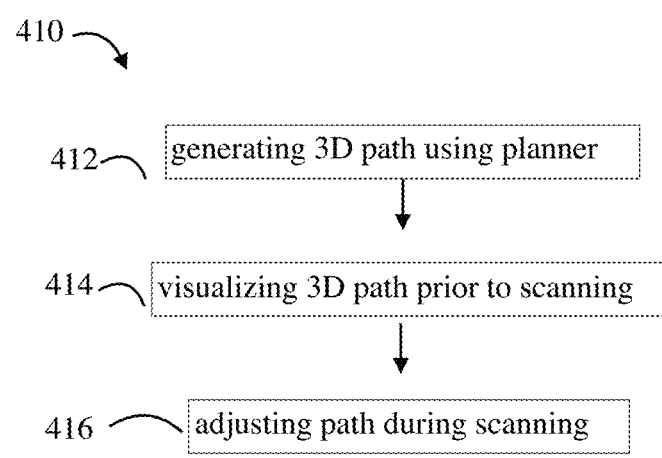
FIG. 4 is a flowchart representation of steps in another preferred method embodiment of the present invention showing the steps of generating a 3D path using a planner, visualizing the 3D path prior to scanning, and adjusting the path during scanning.

FIG. 4 is a flowchart representation of steps in another preferred method embodiment of the present invention showing the steps of Step 412 generating a 3D path using a planner, Step 414 visualizing the 3D path prior to scanning, and Step 416 adjusting the path during scanning.

Figure 5:
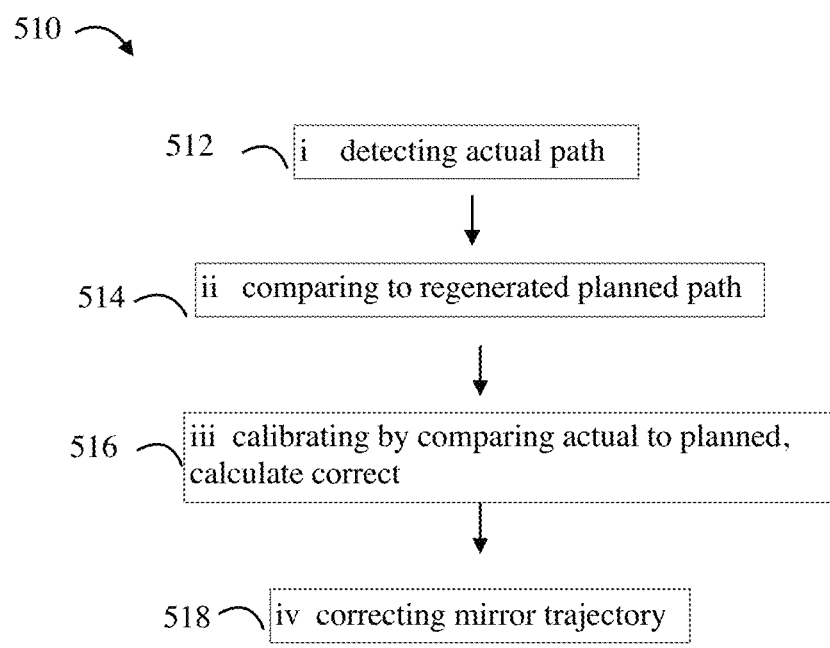
FIG. 5 is a flowchart representation of steps in another preferred method embodiment of the present invention showing the steps of detecting the actual path of the laser being directed by the RGG scanning mirrors, comparing the actual path to a pre-generated planned/optimized path, calibrating by comparing the actual path to the planned path and calculating corrections to the path ROI target coordinates, and correcting the scanning mirrors trajectory(s) to implement the correction(s).

FIG. 5 is a flowchart representation of steps in another preferred method embodiment of the present invention showing the steps of Step 512 detecting the actual path of the laser being directed by the RGG scanning mirrors, Step 514 comparing the actual path to a pre-generated planned/optimized path, Step 516 calibrating by comparing the actual path to the planned path and calculating corrections to the path ROI target coordinates, and Step 518 correcting the scanning mirrors trajectory(s) to implement the correction(s).

Figure 6:
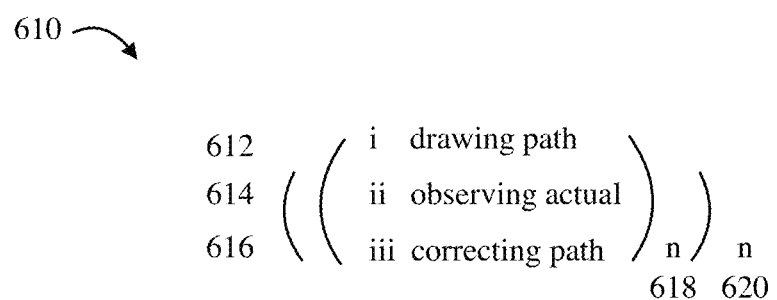
FIG. 6 is a graphic representation of steps in a further preferred method embodiment of the present invention showing the steps of i. drawing a path, ii. observing the actual path, and iii. correcting the path, where the steps are shown in an inner bracket representing that the process may be iterative for an n number of times for a given Frame, along with an outer bracket representing that the iterative process may be automated across an n number of Frames.

FIG. 6 is a graphic representation of steps in a further preferred method embodiment of the present invention showing the steps of Step 612 i. drawing a path, Step 614 ii. observing the actual path, and Step 616 iii. correcting the path, where the steps are shown in an inner bracket 618 representing that the process may be iterative for an n number of times for a given Frame, along with an outer bracket 620 representing that the iterative process may be automated across an n number of Frames.

Figure 7:
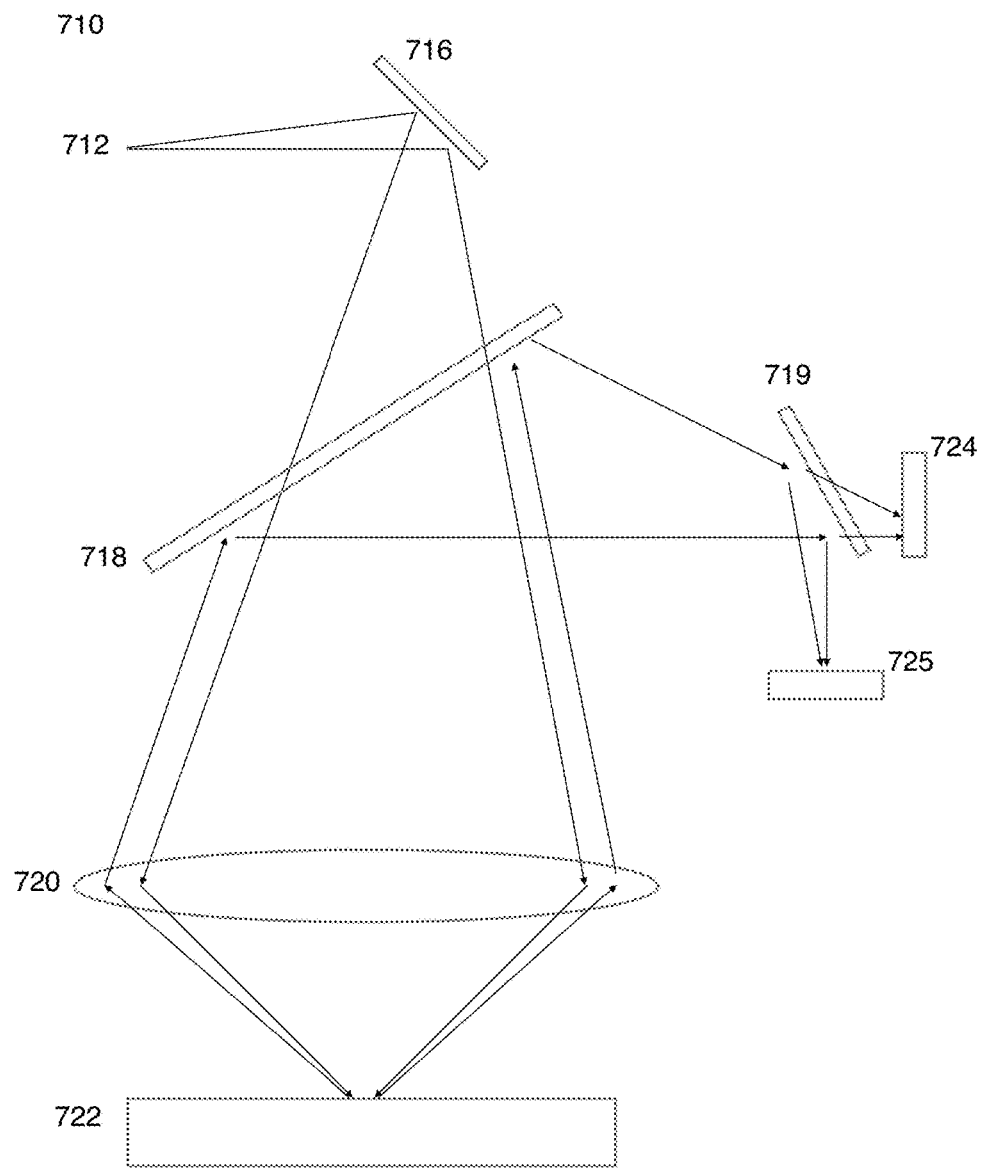
FIG. 7 is a graphic representation of a preferred embodiment of the invention that uses a standard laser path in a standard multi-photon laser microscope where the path optimization method and/or where the calibration method may be used.

FIG. 7 is a graphic representation of a preferred embodiment of the invention that uses a standard laser path in a standard two-photon laser microscope 710 where the path optimization method and/or where the calibration method may be used. FIG. 7 shows a pulsed IR laser 712, a scanning mirror 716, a first dichroic mirror 718, an objective lens 720, a specimen platform 722 having fluorophores at the focal plane, a second dichroic mirror 719, and two photodetectors, a first photodetector 724 configured to detect a first wavelength, a second photodetector 725 configured to detect a second wavelength.

Figure 8:
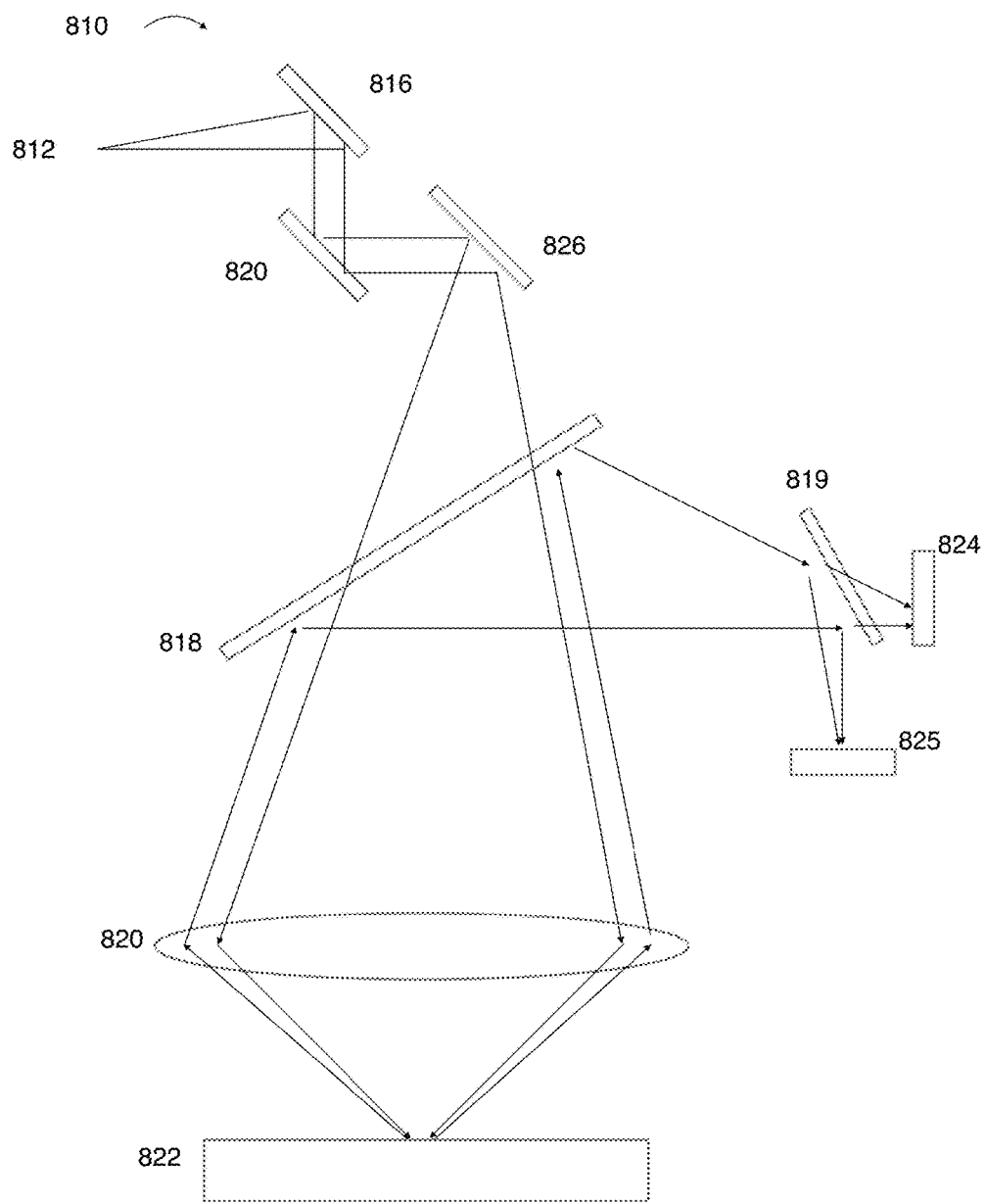
FIG. 8 is a graphic representation of another preferred embodiment of the invention that uses an RGG scanner assembly to achieve high frames rate scanning in a wide field of view, e.g. 5-20 degrees, where the laser path in a high FR multi-photon laser microscope includes a trajectory using a resonant scanner, a first galvanometer scanner, and a second galvanometer scanner, and where the path optimization method and/or where the calibration method may be used.

FIG. 8 is a graphic representation of another preferred embodiment of a high frame rate two-photon laser microscope 810 that uses an RGG scanner assembly to achieve high frame rate scanning in a wide field of view, e.g. 5-20 degrees, where the laser path in a high FR two-photon laser microscope includes a trajectory using a resonant scanner 824, a first galvanometer scanner 820, and a second galvanometer scanner 826, and where the path optimization method and/or where the calibration method may be used. FIG. 8 shows a pulsed IR laser 812, an RGG scanning mirror assembly 824-820-826, a first dichroic mirror 818, an objective lens 820, a specimen platform having fluorophores at the focal plane 822, a second dichroic mirror 819, and two photodetectors, a first photodetector 824 configured to detect a first wavelength, a second photodetector 825 configured to detect a second wavelength.

Figure 9:
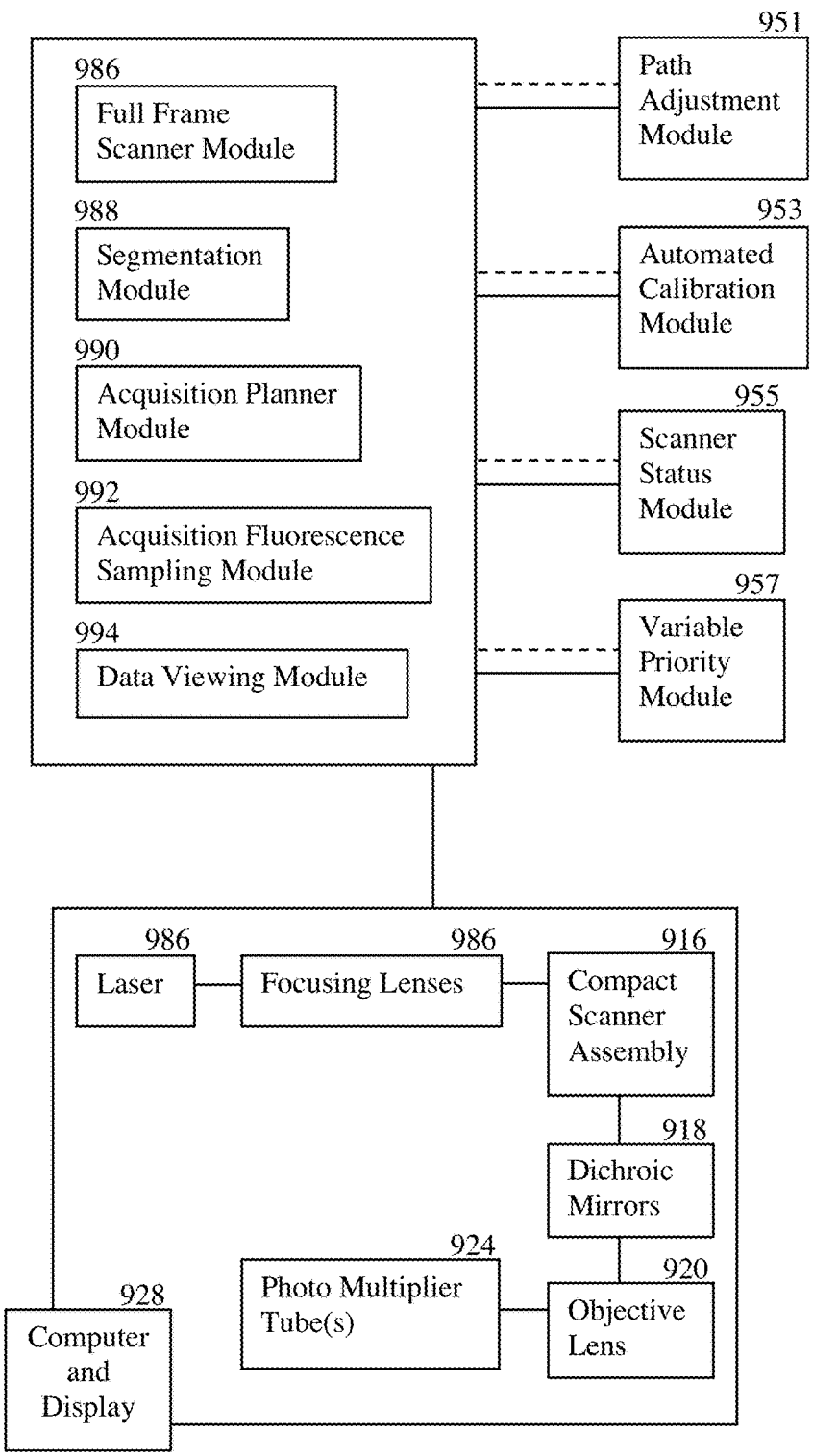
FIG. 9 is a flowchart representation of another preferred adaptive sampling system of the present invention and shows a full frame scanner module, a segmentation module, an acquisition planner module, an acquisition fluorescence sampling module, and a data viewing module in operative association with a multi-photon laser microscope comprising a laser, focusing lenses, a compact scanner assembly, dichroic mirrors, an objective lens, photomultiplier tubes, controlled and processed by a computer for output to a display.

FIG. 9 is a flowchart representation of another preferred adaptive sampling system of the present invention 910 and shows a full frame scanner module 986, a segmentation module 988, an acquisition planner module 990, an acquisition fluorescence sampling module 992, and a data viewing module 994 in operative association with a two-photon laser microscope comprising a laser 912, focusing lenses 914, a compact scanner assembly 916, dichroic mirrors 918, an objective lens 920, photomultiplier tubes 924, controlled and processed by a computer 928 for output to a display. FIG. 9 also shows optional Path Adjustment Module 951, optional Automated Calibration Module 953, optional Scanner Status Module 955, and optional Variable Priority Module 957.

Figure 10:
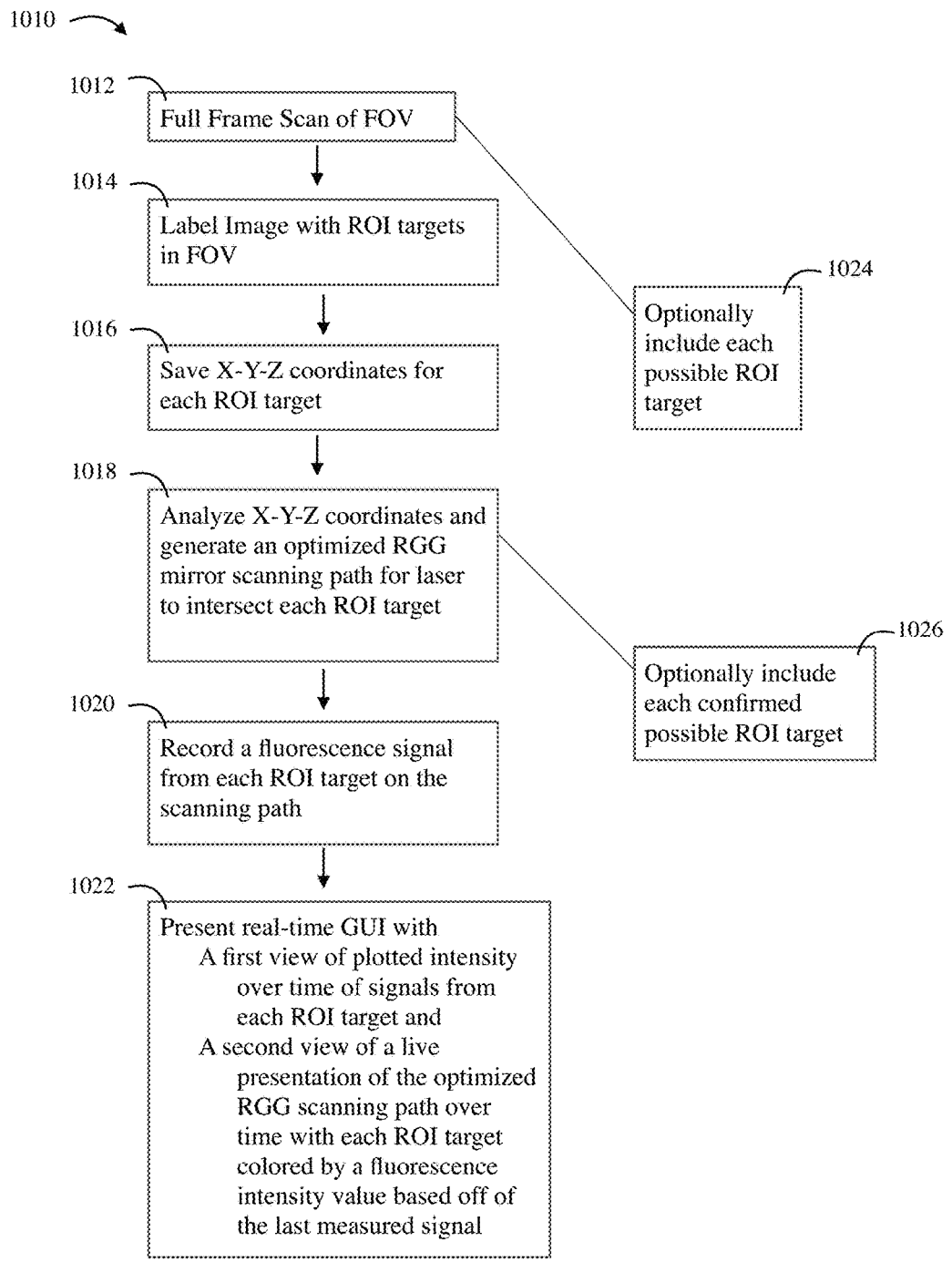
FIG. 10 is a flowchart representation of steps in another preferred method embodiment of the present invention showing scanning, labelling targets, saving coordinates, using a planner to generate an optimized path, recording a signal from each ROI target, and presenting real-time views of intensity and path.

FIG. 10 is a flowchart representation of steps in another preferred method embodiment of the present invention 1010 showing Step 1012 scanning, Step 1014 labelling ROI targets, Step 1016 saving X-Y-Z coordinates for each ROI target, Step 1018 using a planner to generate an optimized path, Step 1020 recording a fluorescence signal from each ROI target, and Step 1022 presenting real-time views of intensity and path. FIG. 10 also shows optional method steps of the invention to Step 1024 vary the signal parameters to include possible ROI targets within a FOV, and Step 1026 to screen the possible ROI targets to include confirmed ROI targets.

Example—Monitoring Specific ROIs Over Time

Figure 11:
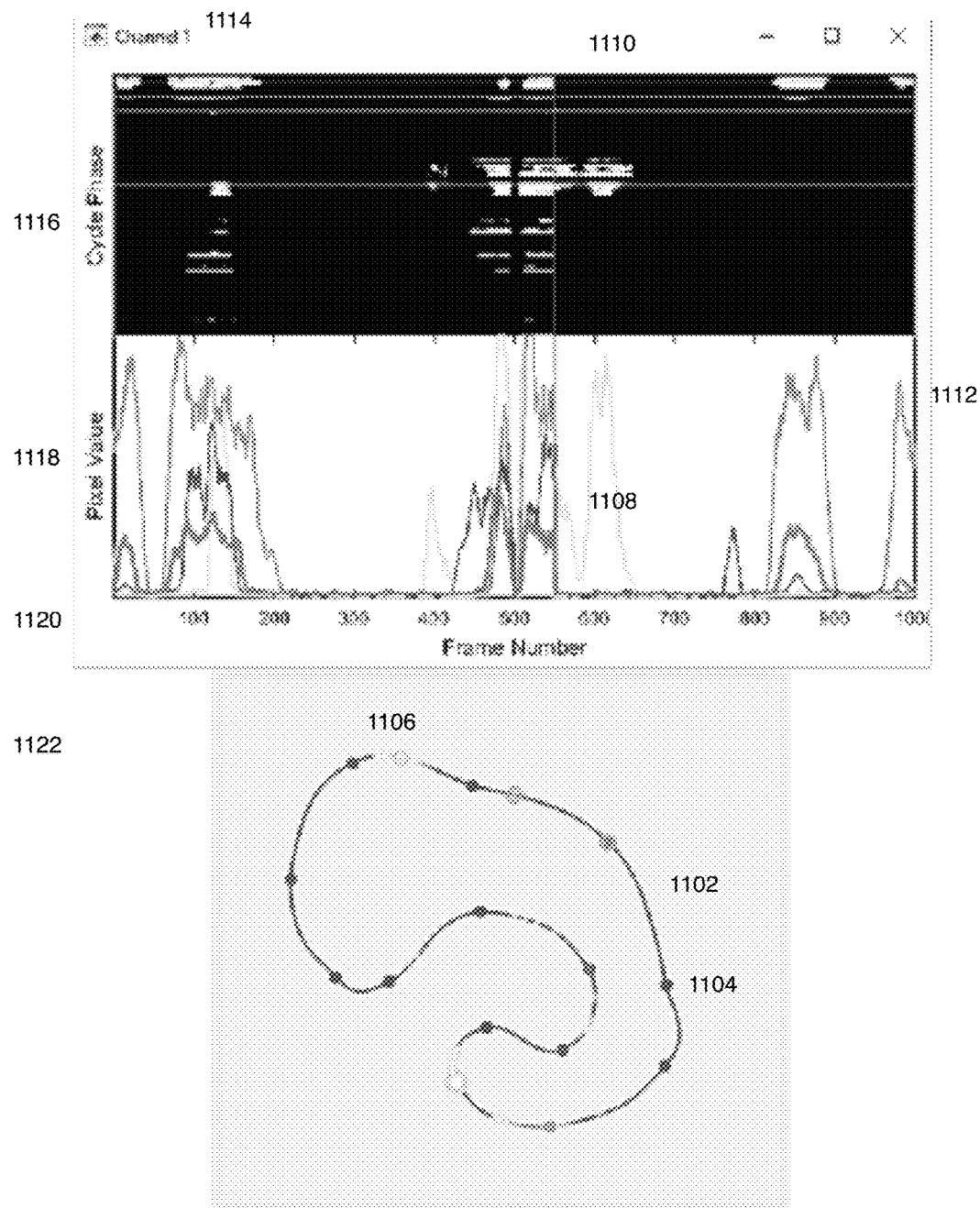
FIG. 11 is a representation of a multi-feature graphical view showing an image of fluorescent signals that have been captured and imaged, plotted over an image of Pixel View by Frame Number of multiple regions of interest (MROIs) being identified, and both of which images correlate to the lower scanner path view with an optimized scanning path based on the MROI points, here shown as circles on the path line.

Referring now to FIG. 11, selective or arbitrary line scanning enables high speed sampling of desired ROIs by reducing time spent scanning areas of little interest in the sample. FIG. 11 shows channel number 1114 which is capturing cycle phase 1116 (top-upper) and Pixel Value 1118 (top-lower) plotted across the Frame Number 1120. Path image 1122 is shown at bottom.

If the locations of desired ROIs have already been identified and are already known, and a user is only interested in how the fluorescence at specified points 1110 is changing over time 1112, an arbitrary or user-optimized path can be configured as taught herein to sample the desired points at high speed, as opposed to raster scanning the entire field which is much slower. Depending on the duration of the scan path 1102 (dictated by the number and spread of ROIs 1104 to be scanned) arbitrary line scanning can sample the entire scan path at rates upwards of 200 Hz, and even MROI scanning up to 2000 Hz, allowing capture of fluorescence transients 1106. The scan path 1102 can be designed in 2D or 3D, enabling use of a fast Z actuator for arbitrary volume scanning. As seen in FIG. 11, in addition to recording fluorescence signals 1108, the line scanning feature includes the ability to record and show in real-time the actual positions of the scan mirrors to ensure that they are accurately hitting the desired ROIs.

In a preferred embodiment, in order to utilize the scan mirror position recording, a second DAQ must be also be deployed, and the galvo position signals must be on a different DAQ than the photo-detector signals.

Figure 12:
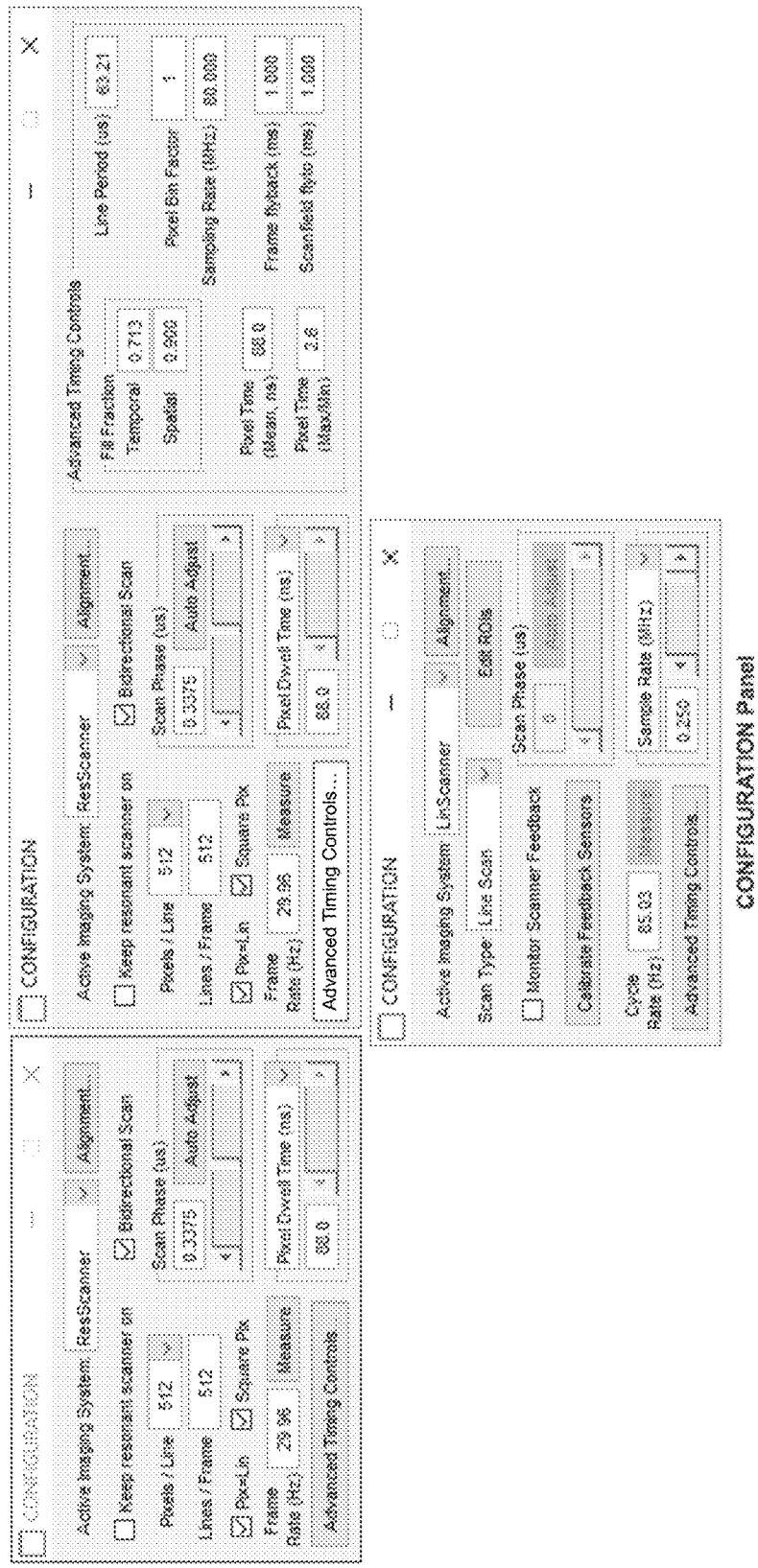
FIG. 12 is a graphical representation of a set of graphical user interfaces that illustrate how a selective optimized scanning embodiment can be configured.

Referring now to FIG. 12, a set of graphical user interfaces illustrate how a selective optimized scanning embodiment can be configured. Initially, a scan path must be configured. At least one scan of the complete path must be completed to identify the ROIs. One scan is referred to as a cycle or frame. Once the ROIs are identified, specific ROIs are chosen as part of a scan path design. Next, a user can opt to determine a specific Cycle Rate interface to determine how frequently to scan the chosen path. The cycle rate indicates how fast cycles can be scanned, which is dictated by the total time duration of the scan path that has been designed.

As shown in FIG. 12, both 2D and 3D scan paths can be designed. The depth aspect, the Z direction, can be controlled by using the FAST Z CONTROLS interface.

Also detailed in FIG. 12, position feedback can be enabled to log to disk and allows showing in real time the actual path scanned by the mirrors. This is useful to ensure the scan mirrors are achieving the desired path. Before using position feedback for the first time, the mirror feedback sensors must be calibrated by clicking Calibrate Feedback Sensors on the CONFIGURATION interface.

Referring further to FIG. 12, the GUI shows a Bidirectional Scan feature that enables two way scanning (ie data is acquired when the X scan mirror is traveling in both directions). Bidirectional scanning will increase the frame rate, while unidirectional scanning can produce higher quality images by avoiding the interlace effect from the phase being slightly incorrect. Even when using unidirectional scanning it is important to have the scan phase properly adjusted to avoid image distortion. Use bidirectional scanning first to get the phase correct then switch over to unidirectional scanning.

Other important features shown in FIG. 12 include Pixels Per Line, and Lines Per Frame.

Constrain Pixels/Line and Lines/Frame to be equal, Square Pix to force individual pixels to have a square aspect ratio, Frame Rate, Scan Phase Adjustment to adjust the timing between acquisition of forward and reverse lines for bidirectional scanning, Pixel Dwell Time, Line Period, Fill Fraction (Temporal/Spatial) to set the fraction of the scanned area in the fast mirror (X) dimension where image acquisition occurs, Pixel Time to obtain mean acquisition time, in ns, for each pixel, Sampling Rate to set the rate that ADC samples are collected, Frame Flyback to control the time to allow for the slow scan mirror (Y) to travel from the end position back to the start position at the end of a frame, Scanfield/Frame Flyto to control the time to allow for the scanner to transition from the end position of one ROI to the start position of another, Scan Type to switch between traditional frame scanning and arbitrary line scanning, Monitor Scanner Feedback to display and record the actual scanner path during arbitrary line scanning, and Calibrate Feedback Sensors to calibrate the position feedback sensor for line scanning. This must be done once for position feedback to work.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine-implemented or computer-implemented at least in part. Some examples can include a tangible computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The abstract is provided to comply with 37 C.F.R. §1.72 (b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment.

The references recited herein are incorporated herein in their entirety, particularly as they relate to teaching the level of ordinary skill in this art and for any disclosure necessary for the commoner understanding of the subject matter of the claimed invention.

The following claims are hereby incorporated into the Detailed Description, with each claim standing on its own as a separate embodiment. It will be clear to a person of ordinary skill in the art that the above embodiments may be altered or that insubstantial changes may be made without departing from the scope of the invention. Accordingly, the scope of the invention is determined by the scope of the following claims and their equitable Equivalents.

The invention claimed is:

1. An automated planner and adaptive sampling system for multi-photon excitation microscopy, comprising:
   a full frame scanner module configured to scan an entire Field of View (FOV) of a specimen and label a detailed high resolution image with multiple Region of Interest (ROI) targets within the FOV;
   a segmentation module configured to save an X-Y-Z coordinate for each ROI target;
   an acquisition planner module configured to analyze the X-Y-Z coordinates for each ROI target, and generate an optimized mirror scanning path for the laser to intersect each ROI target;
   an acquisition fluorescence sampling module configured to use the optimized mirror scanning path and record a fluorescence signal from each ROI target in the FOV;
   a data viewing module configured to present in real time two views with a graphical user interface, a first view comprises a plot of intensity over time of the fluorescent signals from each ROI target, and a second view comprises a live presentation of the optimized mirror scanning path over time period t with each ROI target in the FOV colored by an intensity of fluorescence according to the fluorescent signal last measured at a previous time period t−1;
   a multi-photon excitation microscope for multi-region of interest (MROI) imaging of intact cellular tissue comprising:
      a laser configured for multi-photon laser microscopy;
      a Pockels cell operatively associated with the laser to control laser power;
      one or more focusing lenses in optical communication with the laser;
      a compact scanner assembly in optical communication with the laser;
      one or more dichroic mirrors in optical communication with the laser;
      one or more objective lenses in optical communication with the laser;
      one or more photomultiplier tubes in optical communication with the FOV;
      a computer comprising one or more processors, memory, storage memory, interfaces, controllers, and input devices for operating the multi-photon excitation microscope, said computer having a display for receiving the graphical user interface; wherein the modules comprise computer program instructions executable by the one or more processors.

2. The automated planner and adaptive sampling system of claim 1, wherein the multi-photon excitation microscope is a two-photon excitation microscope.

3. The automated planner and adaptive sampling system of claim 1, wherein the multi-photon excitation microscope is a three-photon excitation microscope.

4. An automated planner and adaptive sampling system for multi-photon excitation microscopy, comprising:
   a full frame scanner module configured to scan an entire Field of View (FOV) of a specimen and label a detailed high resolution image with multiple Region of Interest (ROI) targets within the FOV;
   a segmentation module configured to save an X-Y-Z coordinate for each ROI target;
   an acquisition planner module configured to analyze the X-Y-Z coordinates for each ROI target, and generate an optimized mirror scanning path for the laser to intersect each ROI target;
   an acquisition fluorescence sampling module configured to use the optimized mirror scanning path and record a fluorescence signal from each ROI target in the FOV;
   a data viewing module configured to present in real time two views with a graphical user interface, a first view comprises a plot of intensity over time of the fluorescent signals from each ROI target, and a second view comprises a live presentation of the optimized mirror scanning path over time period t with each ROI target in the FOV colored by an intensity of fluorescence according to the fluorescent signal last measured at a previous time period t−1;
   a multi-photon excitation microscope for multi-region of interest (MROI) imaging of intact cellular tissue comprising:
      a laser configured for multi-photon laser microscopy;
      a Pockels cell operatively associated with the laser to control laser power;
      one or more focusing lenses in optical communication with the laser;
      a compact scanner assembly in optical communication with the laser;
      one or more dichroic mirrors in optical communication with the laser;
      one or more objective lenses in optical communication with the laser;
      one or more photomultiplier tubes in optical communication with the FOV;
      a computer comprising one or more processors, memory, storage memory, interfaces, controllers, and input devices for operating the multi-photon excitation microscope, said computer having a display for receiving the graphical user interface; wherein the modules comprise computer program instructions executable by the one or more processors;

wherein the Frame Rate during wide field of view sampling comprises a range selected from the group of ranges consisting of: Frame Rate range 60 Hz-200 Hz, Frame Rate range 100 Hz-200 Hz, Frame Rate range 100 Hz-500 Hz, Frame Rate range 200 Hz-500 Hz, Frame Rate range 200 Hz-1000 Hz, Frame Rate range 100 Hz-2000 Hz, Frame Rate range 200 Hz-2000 Hz, Frame Rate range 500 Hz-2000 Hz, Frame Rate range 500 Hz-1200 Hz, Frame Rate range 500 Hz-1500 Hz, and Frame Rate range 500 Hz-2000 Hz;

a path adjustment module, said path adjustment module configured to provide a path correction input to change the coordinates of one or more ROI targets within the optimized mirror scanning path;

an automated calibration module configured to generate and save coordinates of an actual mirror scanning path and compare the coordinates of the actual mirror scanning path to the coordinates of the optimized mirror scanning path while a scan is in progress, said automated calibration module configured to adjust the coordinates of the actual mirror scanning path to match the coordinates of the optimized mirror scanning path;

an automated calibration module configured to generate and save coordinates of an actual mirror scanning path and compare the coordinates of the actual mirror scanning path to the coordinates of an updated optimized mirror scanning path while a scan is in progress, said automated calibration module configured to re-scan an entire Field of View (FOV) of a specimen, re-label a detailed high resolution image with multiple Region of Interest (ROI) targets within the FOV, re-save an X-Y-Z coordinate for each ROI target, re-analyze the X-Y-Z coordinates for each ROI target, and generate an updated optimized mirror scanning path for the laser to intersect each ROI target, said automated calibration module configured to adjust the coordinates of the actual mirror scanning path to match the coordinates of the updated optimized mirror scanning path;

a Scanner Status Module configured to generate and save scanner variables while a scan is in progress, said scanner variables comprising scanner motion and scanner orientation for each scanner for each ROI target within a FOV, said Scanner Status Module configured to generate a Scanner Status Report output to the graphical user interface;

a Variable Priority Module configured to generate and save Sampling Variables selected from vertical resolution, horizontal resolution, frame rate, ROI threshold, and laser power, said Variable Priority Module configured to adjust the optimized mirror scanning path for each ROI target within a FOV based on user-selected priority settings of the Sampling Variables, said Variable Priority Module configured to generate a Variable Priority Status Report output to the graphical user interface;

wherein the laser is a femtosecond laser with an emitted wavelength range 680-1400 nm or 760-1100 nm;

wherein the compact scanner assembly comprises a set of electromagnetically actuated scanning mirrors in optical communication with the laser, selected from the group consisting of: a Galvo-Galvo (GG) scanner assembly, an Resonant-Galvo (RG) scanner assembly, a Resonant-Galvo-Galvo (RGG) scanner assembly, a Resonant-Galvo-Galvo-Galvo (RGGG) scanner assembly, a Resonant-Galvo-Galvo-Galvo-Galvo (RGGGG) scanner assembly, and a MEMS mirror scanner assembly;

wherein the compact scanner assembly comprises a set of three electromagnetically actuated scanning mirrors in optical communication with the laser, comprising a first galvanometer scanner (G1) having a mirror (m1), a resonant scanner (R) driven at a resonant frequency selected from 8 KHz, 12 KHz, and 16 KHz, and a second galvanometer scanner (G2) having a mirror (m2), wherein the first galvanometer scanner (G1) and the second galvanometer scanner (G2) are driven by a lower bandwidth control signal specifying an angle for mirror (m1) and for mirror (m2), wherein the set of three scanning mirrors are within a single scanner assembly RGG or GRG, wherein spacing between the first galvanometer scanner (G1) and the resonant scanner (R) ranges from 4.0-12.0 mm, and wherein spacing between the resonant scanner (R) and the second galvanometer scanner (G2) ranges from 4.0-12.0 mm;

wherein the electromagnetically actuated scanning mirrors are controlled by a Piezo/Fast Z control module for controlling the position of the mirrors, and the scanning mirrors are actuated by one or more piezoactuators selected from the group consisting of: a multilayer stack piezoactuator, a monolithic piezoactuator, a tube piezoactuator, a multilayer ring piezoactuator, a bimorph piezoactuator, and a hybrid piezoactuator;

an Equipment Control Module (ECM), said ECM comprising (i) a laser power control unit and a laser wavelength output control in operative association with the laser; and (ii) a galvanometer 1 control, a resonant mirror control, and a galvanometer 2 control in operative association with the scanning mirrors;

a Data Acquisition Module (DAQ), said DAQ comprising a frame rate control module, a scan mode control module, a scan zoom control module, and a data acquisition pixel density control module in operative association with the DAQ;

a dichroic mirror light path adjustment module in operative association with the one or more dichroic mirrors;

wherein the one or more dichroic mirrors is positioned after the scanning mirrors in optical communication with the laser, wherein the dichroic mirrors are reflective at a first lower wavelength, and the mirrors are transmissive at a second wavelength higher than the first wavelength;

wherein the one or more dichroic mirrors are reflective at a wavelength of less than 680 nm and the mirrors are transmissive at a wavelength ranging from 680-1400 nm, or wherein the one or more dichroic mirrors are reflective at a wavelength of less than 760 nm and the mirrors are transmissive at a wavelength ranging from 760-1100 nm;

wherein the one or more objective lenses have a pupil diameter from 10-30 mm configured to output the emitted laser to interact with a specimen, and configured to receive an excitation illumination at the second wavelength;

wherein the one or more photomultiplier tubes comprise at least two non-descanned Photo Multiplier Tubes configured to receive excitation illumination and configured with a transimpedance amplifier to transmit image data thru a controller interface to a Data Acquisition Module;

wherein the Data Acquisition (DAQ) Module has a channel digitizer having from 2-32 channels, an Field Programmable Gate Array (FPGA) module, and a Pockels control module, wherein the computer is connected to the DAQ, the computer comprising a central processing unit (CPU) configured to process in 64-bit, in Quad-core and 3.5 GHZ or better, Random Access Memory (RAM) at least 8 GB, a Graphics Processing Unit (GPU), two or more PCIe slots, and a storage memory comprising an Solid State Drive (SSD) or a Hard Drive;

an Experimental Control Module, comprising (i) a data acquisition parameters control module in operative association with the DAQ, (ii) a MROI control module in operative association with the DAQ, (iii) a custom acquisition programming module in operative association with the DAQ; and, (iv) a camera port control in operative association with the DAQ;

a Data Analysis Module (DAQ), comprising (i) an Image dimension module in operative association with the DAQ, (ii) an image resolution module in operative association with the DAQ, (iii) a color assignment by channel module in operative association with the DAQ, (iv) a 3D reconstruction generation module in operative association with the DAQ, and (v) a storage control module in operative association with the DAQ;

a BigTiff module in operative association with the DAQ, and an Image acquisition software suite module configured to process image data and generate TIFF files from said image data;

wherein the Piezo/Fast Z control module for controlling the position of the mirrors controls the position of the mirrors in three dimensional planes X-Y-Z, wherein the laser is configured as a point spread function (PSF) in a three-dimensional hourglass shape at the specimen, and wherein the Piezo/Fast Z control module is configured to move the point spread function in the Z direction to drive the PSF into the specimen;

wherein the full frame scanner module is configured to scan an entire Field of View (FOV) of a specimen and label a detailed high resolution image with multiple possible Region of Interest (ROI) targets within the FOV;

wherein the segmentation module is configured to screen the possible ROI targets using an automated segmentation module to locate and confirm targets within the FOV, and to save an X-Y-Z coordinate for each confirmed ROI target;

wherein the acquisition planner module is configured to analyze the X-Y-Z coordinates for each confirmed ROI target, and generate an optimized RGG mirror scanning path for the laser to intersect each ROI target and each confirmed ROI target;

wherein the acquisition fluorescence sampling module is configured to use the optimized RGG mirror scanning path and record a fluorescence signal from each confirmed ROI target in the FOV;

wherein the data viewing module is configured to present in real time two views with the graphical user interface, the first view further comprising a plot of intensity over time of the fluorescent signals from each confirmed ROI target, and the second view further comprising a live presentation of the optimized RGG mirror scanning path over time period t with each confirmed ROI target in the FOV colored by an intensity of fluorescence according to the fluorescent signal last measured at a previous time period t−1;

an automated threshold trigger module, said automated threshold trigger module configured to add coordinates of one or more ROI targets within the optimized RGG mirror scanning path based on a triggering event, said automated threshold trigger module further configured to generate and save a series of image Frames based on the triggering event;

wherein the Sampling Rate during wide field of view sampling ranges from 80 MHz-10 GHz;

wherein the multi-photon excitation microscope comprises one or more relay lenses in optical communication with the laser.

5. The automated planner and adaptive sampling system of claim 4, further comprising a third galvanometer scanner (G3) and mirror (m3) within the single scanner assembly (RGGG), wherein the third galvanometer scanner (G3) is driven by a lower bandwidth control signal specifying an angle for mirror (m3), wherein spacing between the second galvanometer scanner (G2) and the third galvanometer scanner (G3) ranges from 4.0-12.0 mm.

6. A method for adaptive sampling to maintain a high frame rate during wide field of view sampling in a system for multi-photon excitation microscopy, comprising the steps:

performing a full frame scan of an entire Field of View (FOV) of a specimen and labelling a detailed high resolution image with multiple Region of Interest (ROI) targets within the FOV;

saving an X-Y-Z coordinate for each ROI target;

analyzing the X-Y-Z coordinates for each ROI target, and generating an optimized mirror scanning path for the laser to intersect each ROI target;

using the optimized mirror scanning path and recording a fluorescence signal from each ROI target in the FOV;

presenting in real time two views with a graphical user interface, a first view comprises a plot of intensity over time of the fluorescent signals from each ROI target, and a second view comprises a live presentation of the optimized mirror scanning path over time period t with each ROI target in the FOV colored by an intensity of fluorescence according to the fluorescent signal last measured at a previous time period t−1;

wherein the multi-photon excitation microscope for multi-region of interest (MROI) imaging of intact cellular tissue comprises:
 a laser configured for multi-photon laser microscopy;
 a Pockels cell operatively associated with the laser to control laser power;
 one or more focusing lenses in optical communication with the laser;
 a compact scanner assembly in optical communication with the laser;
 one or more dichroic mirrors in optical communication with the laser;
 one or more objective lenses in optical communication with the laser;
 one or more photomultiplier tubes in optical communication with the FOV;
 a computer comprising one or more processors, memory, storage memory, interfaces, controllers, and input devices for operating the multi-photon excitation microscope, said computer having a display for receiving the graphical user interface;
 wherein the modules comprise computer program instructions executable by the one or more processors.

7. The method of claim 6,
wherein the step of performing a full frame scan of an entire Field of View (FOV) of a specimen and labelling a detailed high resolution image with multiple Region of Interest (ROI) targets within the FOV, further comprises the step of labelling possible targets within the FOV, and labelling and storing the possible targets as a Region of Interest (ROI);
wherein the step of saving an X-Y-Z coordinate for each ROI target, further comprises the step of screening the ROIs using an automated segmentation module to locate and confirm possible ROI targets within the FOV before saving an X-Y-Z coordinate for each confirmed ROI target;
wherein the step of analyzing the X-Y-Z coordinates for each ROI target, and generating an optimized mirror scanning path for the laser to intersect each ROI target, further comprises the steps of analyzing the X-Y-Z coordinates for each of the confirmed ROI targets using an acquisition planner, and generating an optimized RGG mirror scanning path for the laser to intersect each ROI target and each confirmed ROI target;
wherein the step of using the optimized mirror scanning path and recording a fluorescence signal from each ROI target in the FOV, further comprises the step of using the optimized mirror scanning path and recording a fluorescence signal from each confirmed ROI target in the FOV;
wherein the step of presenting in real time two views with the graphical user interface, further comprises a first view that includes a plot of intensity over time of the fluorescent signals from each confirmed ROI target, and a second view that includes a live presentation of the optimized mirror scanning path over time period t with each confirmed ROI target in the FOV colored by an intensity of fluorescence according to the fluorescent signal last measured at a previous time period t−1;
wherein the Frame Rate comprises a range selected from the group of ranges consisting of: Frame Rate range 60 Hz-200 Hz, Frame Rate range 100 Hz-200 Hz, Frame Rate range 100 Hz-500 Hz, Frame Rate range 200 Hz-500 Hz, Frame Rate range 200 Hz-1000 Hz, Frame Rate range 100 Hz-2000 Hz, Frame Rate range 200 Hz-2000 Hz, Frame Rate range 500 Hz-2000 Hz, Frame Rate range 500 Hz-1200 Hz, Frame Rate range 500 Hz-1500 Hz, and Frame Rate range 500 Hz-2000 Hz;
wherein the method uses a Sampling Rate during wide field of view sampling ranges from 80 MHz-10 GHz.

8. The method of claim 6, further comprising the step of switching from line scanning to frame scanning of a region of the FOV when the fluorescence signal exceeds a pre-set threshold.

9. The method of claim 6, further comprising the step of providing a path correction input to change the coordinates of one or more ROI targets within the optimized mirror scanning path.

10. The method of claim 6, further comprising the step of automatically calibrating a scanning path by generating and saving coordinates of an actual RGG mirror scanning path and comparing the coordinates of the actual mirror scanning path to the coordinates of the optimized mirror scanning path while a scan is in progress, and adjusting the coordinates of the actual mirror scanning path to match the coordinates of the optimized mirror scanning path.

11. The method of claim 6, further comprising the step of automatically calibrating a scanning path by generating and saving coordinates of an actual mirror scanning path and comparing the coordinates of the actual mirror scanning path to the coordinates of an updated optimized mirror scanning path while a scan is in progress, and re-scanning an entire Field of View (FOV) of a specimen, re-labelling a detailed high resolution image with multiple Region of Interest (ROI) targets within the FOV, re-saving an X-Y-Z coordinate for each ROI target, re-analyzing the X-Y-Z coordinates for each ROI target, and generating an updated optimized mirror scanning path for the laser to intersect each ROI target, and adjusting the coordinates of the actual mirror scanning path to match the coordinates of the updated optimized mirror scanning path.

12. The method of claim 6, further comprising the steps of generating and saving scanner variables while a scan is in progress, said scanner variables comprising scanner motion and scanner orientation for each scanner for each ROI target within a FOV, said Scanner Status Module configured to generate a Scanner Status Report output to the graphical user interface.

13. The method of claim 6, further comprising the steps of generating and saving Sampling Variables selected from vertical resolution, horizontal resolution, frame rate, ROI threshold, and laser power, and adjusting the optimized mirror scanning path for each ROI target within a FOV based on user-selected priority settings of the Sampling Variables, and generating a Variable Priority Status Report output to the graphical user interface.

14. The method of claim 6, further comprising the steps of triggering an automated threshold trigger by adding coordinates of one or more ROI targets within the optimized mirror scanning path in response to a triggering event, and generating and saving a series of image Frames in response to the triggering event.

15. The method of claim 6, wherein the multi-photon excitation microscope is a two-photon excitation microscope or a three-photon excitation microscope.

16. The method of claim 6, wherein the multi-photon excitation microscope comprises one or more relay lenses in optical communication with the laser.

17. The method of claim 6, wherein the compact scanner assembly comprises a set of electromagnetically actuated scanning mirrors in optical communication with the laser, selected from the group consisting of: a Galvo-Galvo (GG) scanner assembly, an Resonant-Galvo (RG) scanner assembly, a Resonant-Galvo-Galvo (RGG) scanner assembly, a Resonant-Galvo-Galvo-Galvo (RGGG) scanner assembly, a Resonant-Galvo-Galvo-Galvo-Galvo (RGGGG) scanner assembly, and a MEMS mirror scanner assembly.

18. The method of claim 6, wherein the compact scanner assembly comprises a set of three electromagnetically actuated scanning mirrors in optical communication with the laser, comprising in sequence a resonant scanner (R) driven at a resonant frequency selected from 8 KHz, 12 KHz, and 16 KHz, a first galvanometer scanner (G1), and a second galvanometer scanner (G2).

* * * * *

UNITED STATES PATENT AND TRADEMARK OFFICE
CERTIFICATE OF CORRECTION

PATENT NO. : 9,939,381 B1
APPLICATION NO. : 15/481476
DATED : April 10, 2018
INVENTOR(S) : Bruce Kimmel et al.

It is certified that error appears in the above-identified patent and that said Letters Patent is hereby corrected as shown below:

Column 1, Line 12, please insert:
--This invention was made with government support under contract R43 MH110021 awarded by National Institute of Health. The government has certain rights in the invention.--

Signed and Sealed this
Twenty-ninth Day of May, 2018

Andrei Iancu
*Director of the United States Patent and Trademark Office*